(12) United States Patent
Lee et al.

(10) Patent No.: US 8,993,128 B2
(45) Date of Patent: Mar. 31, 2015

(54) HETEROCYCLIC COMPOUND AND ORGANIC LIGHT-EMITTING DEVICE CONTAINING SAME

(75) Inventors: Sun-Young Lee, Yongin (KR); Seok-Hwan Hwang, Yongin (KR); Young-Kook Kim, Yongin (KR); Yoon-Hyun Kwak, Yongin (KR); Hye-Jin Jung, Yongin (KR); Jin-O Lim, Yongin (KR); Jong-Hyuk Lee, Yongin (KR); Sang-Hyun Han, Yongin (KR); Se-Jin Cho, Yongin (KR)

(73) Assignee: Samsung Display Co., Ltd., Yongin, Gyeonggi-Do (KR)

( * ) Notice: Subject to any disclaimer, the term of this patent is extended or adjusted under 35 U.S.C. 154(b) by 498 days.

(21) Appl. No.: 13/326,402

(22) Filed: Dec. 15, 2011

(65) Prior Publication Data

US 2012/0319087 A1 Dec. 20, 2012

(30) Foreign Application Priority Data

Jun. 16, 2011 (KR) ........................ 10-2011-0058633

(51) Int. Cl.
*H01L 51/54* (2006.01)
*C07D 471/04* (2006.01)
(Continued)

(52) U.S. Cl.
CPC ............ *C07D 221/18* (2013.01); *C07D 401/14* (2013.01); *C07D 401/10* (2013.01);
(Continued)

(58) Field of Classification Search
None
See application file for complete search history.

(56) References Cited

U.S. PATENT DOCUMENTS

| 5,635,308 A | 6/1997 | Inoue et al. |
| 5,645,948 A | 7/1997 | Shi et al. |

(Continued)

FOREIGN PATENT DOCUMENTS

| JP | 8-12600 A | 1/1996 |
| JP | 2000-003782 A | 1/2000 |

(Continued)

OTHER PUBLICATIONS

Campbell et al. (J. Chem. Soc. 1957, p. 207).*

(Continued)

*Primary Examiner* — J. L. Yang
(74) *Attorney, Agent, or Firm* — Lee & Morse, P.C.

(57) ABSTRACT

A heterocyclic compound, organic light-emitting device, and a flat panel display device, the heterocyclic compound being represented by Formula 1 or 2 below:

Formula 1

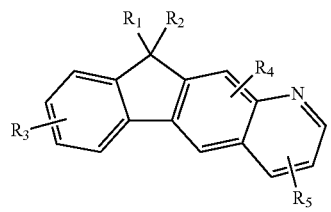

Formula 2

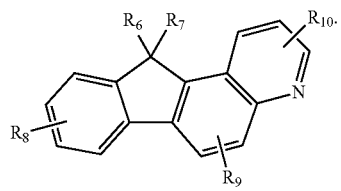

13 Claims, 1 Drawing Sheet

(51) Int. Cl.
| | |
|---|---|
| C07D 409/10 | (2006.01) |
| C07D 401/10 | (2006.01) |
| C07D 221/18 | (2006.01) |
| C07D 401/14 | (2006.01) |
| C09K 11/06 | (2006.01) |
| H01L 51/00 | (2006.01) |
| H01L 51/50 | (2006.01) |

(52) U.S. Cl.
 CPC ............ C07D409/10 (2013.01); C07D 471/04 (2013.01); C09K 11/06 (2013.01); H01L 51/0072 (2013.01); *H01L 51/5012* (2013.01); *C09K 2211/1029* (2013.01); *C09K 2211/1044* (2013.01); *C09K 2211/1092* (2013.01)
 USPC ........................... 428/690; 544/180; 544/333

(56) References Cited

U.S. PATENT DOCUMENTS

| | | | |
|---|---|---|---|
| 5,972,247 | A | 10/1999 | Shi et al. |
| 6,465,115 | B2 | 10/2002 | Shi et al. |
| 6,596,415 | B2 | 7/2003 | Shi et al. |
| 2007/0003783 | A1 | 1/2007 | Morishita et al. |
| 2010/0140604 | A1* | 6/2010 | Yamada et al. ................ 257/40 |
| 2011/0031483 | A1 | 2/2011 | Kwak et al. |

FOREIGN PATENT DOCUMENTS

| | | | | |
|---|---|---|---|---|
| KR | 10-2006-0007022 A | 1/2006 | | |
| KR | 10-2008-0044160 A | 5/2008 | | |
| KR | 10-2010-0003624 A | 1/2010 | | |
| KR | 10-2010-0073543 A | 7/2010 | | |
| KR | 10-2011-0016031 A | 2/2011 | | |
| WO | WO2010062010 A1 * | 6/2010 | ............. | C09K 11/06 |

OTHER PUBLICATIONS

Tang, C.W., et al., "Organic electroluminescent diodes," *Applied Physics Letters*, vol. 51, Issue 12, Sep. 21, 1987, pp. 913-915.

Adachi, Chihaya, et al., "Confinement of charge carriers and molecular excitons within 5-nm-thick emitter layer in organic electroluminescent devices with a double heterostructure," *Applied Physics Letters*, vol. 57, Issue 6, Aug. 6, 1990, pp. 531-533.

Sakamoto, Youichi, et al., "Synthesis, Characterization, and Electron-Transport Property of Perfluorinated Phenylene Dendrimers," *Journal of the American Chemical Society*, vol. 122, 2000, pp. 1832-1833.

Yamaguchi, S., et al., "Diphenylamino-Substituted 2,5-Diarylsiloles for Single-Layer Organic Electroluminescent Devices," *Chemistry Letters*, 2001, pp. 98-99.

* cited by examiner

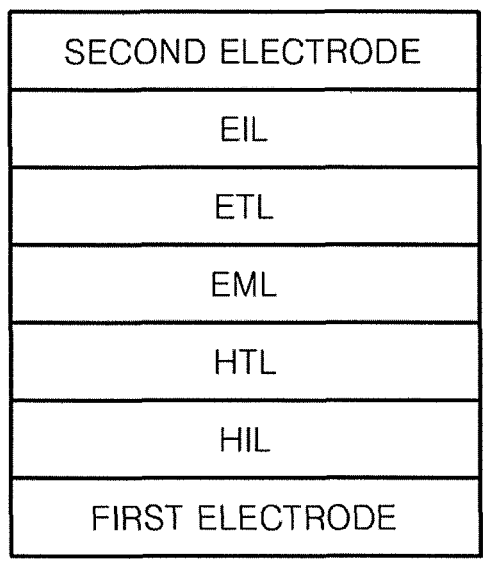

HETEROCYCLIC COMPOUND AND ORGANIC LIGHT-EMITTING DEVICE CONTAINING SAME

CROSS-REFERENCE TO RELATED PATENT APPLICATION

This application claims the benefit of Korean Patent Application No. 10-2011-0058633, filed on Jun. 16, 2011, in the Korean Intellectual Property Office, the disclosure of which is incorporated herein in its entirety by reference.

BACKGROUND

1. Field

Embodiments relate to a heterocyclic compound and an organic light-emitting device including the heterocyclic compound.

2. Description of the Related Art

Light-emitting devices are self-emission type display devices that have a wide viewing angle, a high contrast ratio, and a short response time. Due to these characteristics, light-emitting devices are drawing more attention. Such light-emitting devices may be roughly classified into inorganic light-emitting devices that include emission layers containing inorganic compounds, and organic light-emitting devices that include emission layers containing organic compounds. For example, organic light-emitting devices may have higher brightness, lower driving voltages, and shorter response times than inorganic light-emitting devices, and may render multi-colored displays. Thus, much research into such organic light-emitting devices has been conducted. Generally, an organic light-emitting device may have a stack structure including an anode, a cathode, and an organic emission layer interposed therebetween. However, a hole injection layer and/or a hole transport layer may be further stacked between the anode and the organic emission layer, and/or an electron transport layer may be further stacked between the organic emission layer and the cathode. For example, an organic light-emitting device may have a stack structure of anode/hole transport layer/organic emission layer/cathode or a stack structure of anode/hole transport layer/organic emission layer/electron transport layer/cathode.

SUMMARY

The present invention also provides an organic light-emitting device including the heterocyclic compound.

The present invention also provides a flat panel display device including the organic light-emitting device.

According to an aspect of the present invention, there is provided a heterocyclic compound represented by Formula 1 below:

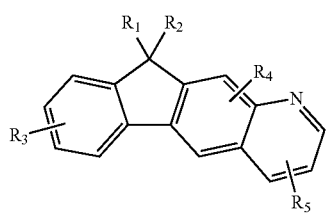

Formula 1 wherein $R_1$ to $R_5$ are each independently selected from the group consisting of a hydrogen atom, a heavy hydrogen atom, a substituted or unsubstituted C1-C60 alkyl group, a substituted or unsubstituted C2-C60 alkenyl group, a substituted or unsubstituted C2-C60 alkynyl group, a substituted or unsubstituted C3-C60 cycloalkyl group, a substituted or unsubstituted C1-C60 alkoxy group, a substituted or unsubstituted C5-C60 aryloxy group, a substituted or unsubstituted C5-C60 arylthio group, a substituted or unsubstituted C5-C60 aryl group, an amino group substituted with a C5-C60 aryl group or a C3-C60 heteroaryl group, a substituted or unsubstituted C3-C60 heteroaryl group, a substituted or unsubstituted C6-C60 condensed polycyclic group, a halogen atom, a cyano group, a nitro group, a hydroxy group, and a carboxy group.

According to another aspect of the present invention, there is provided a heterocyclic compound represented by Formula 2 below:

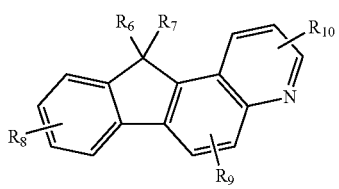

Formula 2 wherein $R_6$ to $R_{10}$ are each independently selected from the group consisting of a hydrogen atom, a heavy hydrogen atom, a substituted or unsubstituted C1-C60 alkyl group, a substituted or unsubstituted C2-C60 alkenyl group, a substituted or unsubstituted C2-C60 alkynyl group, a substituted or unsubstituted C3-C60 cycloalkyl group, a substituted or unsubstituted C1-C60 alkoxy group, a substituted or unsubstituted C5-C60 aryloxy group, a substituted or unsubstituted C5-C60 arylthio group, a substituted or unsubstituted C5-C60 aryl group, an amino group substituted with a C5-C60 aryl group or a C3-C60 heteroaryl group, a substituted or unsubstituted C3-C60 heteroaryl group, a substituted or unsubstituted C6-C60 condensed polycyclic group, a halogen atom, a cyano group, a nitro group, a hydroxy group, and a carboxy group.

$R_1$ to $R_{10}$ may be each independently selected from the group consisting of a hydrogen atom, a heavy hydrogen atom, a cyano group, a halogen atom, a substituted or unsubstituted C1-C20 alkyl group, a substituted or unsubstituted C5-C40 aryl group, a substituted or unsubstituted C3-C40 heteroaryl group, an amino group substituted with a C5-C40 aryl group or a C3-C20 heteroaryl group, and a substituted or unsubstituted C6-C40 condensed polycyclic group.

$R_1$ to $R_{10}$ may be each independently selected from the group consisting of a hydrogen atom, a heavy hydrogen atom, a halogen atom, a cyano group, a C1-C20 alkyl group, and compounds represented by Formulae 2a to 2g below:

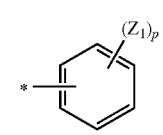

2a

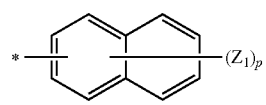

2b

-continued

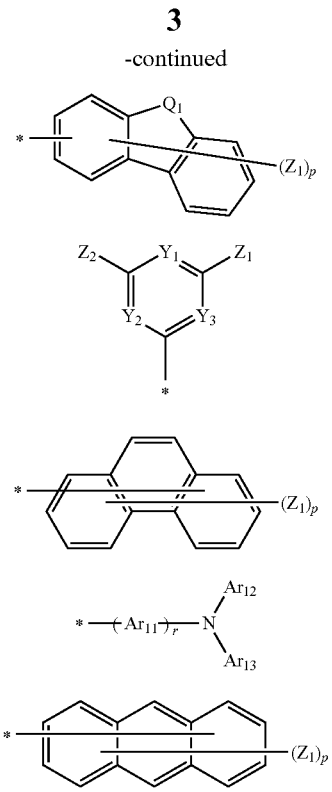

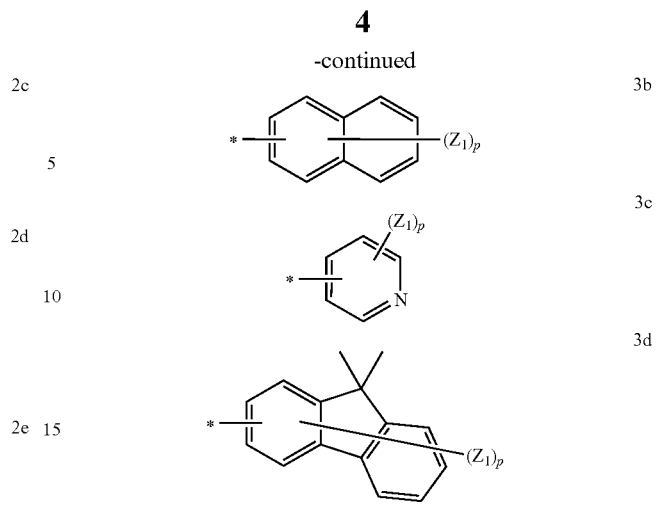

wherein $Q_1$ is selected from the group consisting of linking groups represented by $-C(R_{11})(R_{12})-$, $-N(R_{13})-$, $-S-$, and $-O-$;

$Y_1$, $Y_2$, and $Y_3$ are each independently selected from the group consisting of linking groups represented by $-N=$ and $-C(R_{14})=$;

$Z_1$, $Z_2$, $Ar_{12}$, $Ar_{13}$, $R_{11}$, $R_{12}$, and $R_{13}$ are each independently selected from the group consisting of a hydrogen atom, a heavy hydrogen atom, a substituted or unsubstituted C1-C20 alkyl group, a substituted or unsubstituted C5-C20 aryl group, a substituted or unsubstituted C3-C20 heteroaryl group, a substituted or unsubstituted C6-C20 condensed polycyclic group, a halogen atom, a cyano group, a nitro group, a hydroxy group, and a carboxy group;

$Ar_{11}$ is selected from the group consisting of a substituted or unsubstituted C1-C20 alkylene group, a substituted or unsubstituted C5-C20 arylene group, and a substituted or unsubstituted C3-C20 heteroarylene group;

p is an integer from 1 to 12;

r is an integer from 0 to 5; and

* is a binding site.

$R_1$ to $R_{10}$ may be each independently selected from the group consisting of a hydrogen atom, a heavy hydrogen atom, a halogen atom, a cyano group, a methyl group, an ethyl group, a propyl group, a butyl group, a pentyl group, and compounds represented by Formulae 3a to 3d below:

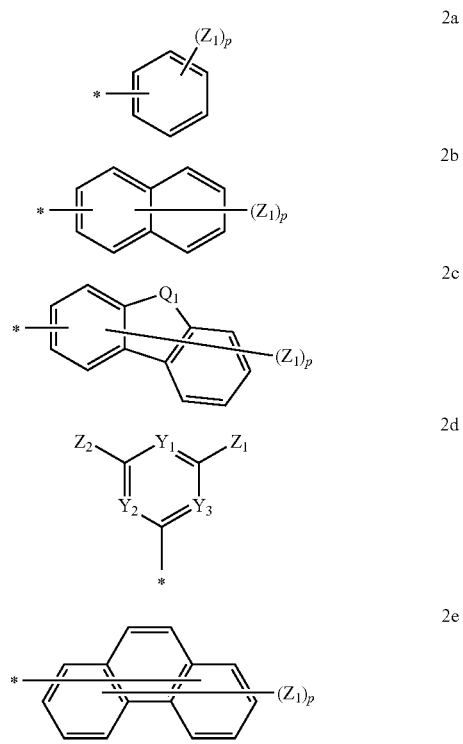

wherein $Z_1$ is selected from the group consisting of a hydrogen atom, a heavy hydrogen atom, a substituted or unsubstituted C1-C20 alkyl group, a substituted or unsubstituted C5-C20 aryl group, a substituted or unsubstituted C3-C20 heteroaryl group, a substituted or unsubstituted C6-C20 condensed polycyclic group, a halogen atom, a cyano group, a nitro group, a hydroxy group, and a carboxy group;

p is an integer from 1 to 12; and

* is a binding site.

$R_1$, $R_2$, $R_6$, and $R_7$ may be each independently selected from the group consisting of a hydrogen atom, a heavy hydrogen atom, a substituted or unsubstituted C1-C20 alkyl group, a substituted or unsubstituted C5-C20 aryl group, and $R_3$, $R_4$, $R_5$, $R_8$, $R_9$, and $R_{10}$ are each independently selected from the group consisting of a hydrogen atom, a heavy hydrogen atom, a halogen atom, a cyano group, a C1-C20 alkyl group, and compounds represented by Formulae 2a to 2g below:

-continued

2f

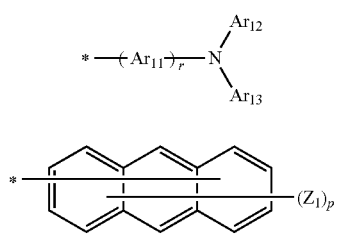

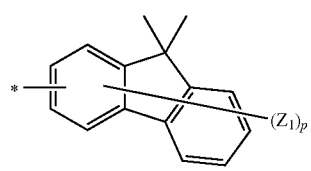

2g wherein $Q_1$ is selected from the group consisting of linking groups represented by $-C(R_{11})(R_{12})-$, $-N(R_{13})-$, $-S-$, and $-O-$;

$Y_1$, $Y_2$, and $Y_3$ are each independently selected from the group consisting of linking groups represented by $-N=$ and $-C(R_{14})=$;

$Z_1$, $Z_2$, $Ar_{12}$, $Ar_{13}$, $R_{11}$, $R_{12}$, and $R_{13}$ are each independently selected from the group consisting of a hydrogen atom, a heavy hydrogen atom, a substituted or unsubstituted C1-C20 alkyl group, a substituted or unsubstituted C5-C20 aryl group, a substituted or unsubstituted C3-C20 heteroaryl group, a substituted or unsubstituted C6-C20 condensed polycyclic group, a halogen atom, a cyano group, a nitro group, a hydroxy group, and a carboxy group;

$Ar_{11}$ is selected from the group consisting of a substituted or unsubstituted C1-C20 alkylene group, a substituted or unsubstituted C5-C20 arylene group, and a substituted or unsubstituted C3-C20 heteroarylene group;

p is an integer from 1 to 12; and r is an integer from 0 to 5; and

* is a binding site.

$R_1$, $R_2$, $R_4$, $R_5$, $R_6$, $R_7$, $R_9$, and $R_{10}$ may be each independently selected from the group consisting of a hydrogen atom, a heavy hydrogen atom, a substituted or unsubstituted C1-C20 alkyl group, and a substituted or unsubstituted C5-C20 aryl group, and $R_3$ and $R_8$ are each independently selected from the group consisting of a hydrogen atom, a heavy hydrogen atom, a halogen atom, a cyano group, a methyl group, an ethyl group, a propyl group, a butyl group, a pentyl group, and compounds represented by Formulae 3a to 3d below:

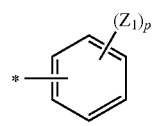

3a

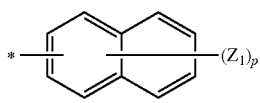

3b

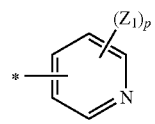

3c wherein $Z_1$ is selected from the group consisting of a hydrogen atom, a heavy hydrogen atom, a substituted or unsubstituted C1-C20 alkyl group, a substituted or unsubstituted C5-C20 aryl group, a substituted or unsubstituted C3-C20 heteroaryl group, a substituted or unsubstituted C6-C20 condensed polycyclic group, a halogen atom, a cyano group, a nitro group, a hydroxy group, and a carboxy group;

p is an integer from 1 to 12; and

* is a binding site.

$R_1$, $R_2$, $R_6$, and $R_7$ may be each independently a methyl group or a phenyl group, and $R_3$, $R_4$, $R_5$, $R_8$, $R_9$, and $R_{10}$ are each independently selected from the group consisting of a hydrogen atom, a heavy hydrogen atom, a halogen atom, a cyano group, a methyl group, an ethyl group, a propyl group, a butyl group, a pentyl group, and compounds selected from the group consisting of Formulae 3a to 3d below:

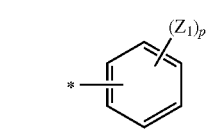

3a

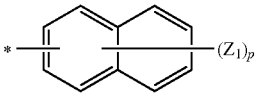

3b

3c

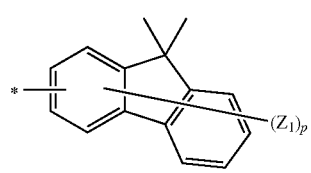

3d wherein $Z_1$ is selected from the group consisting of a hydrogen atom, a heavy hydrogen atom, a substituted or unsubstituted C1-C20 alkyl group, a substituted or unsubstituted C5-C20 aryl group, a substituted or unsubstituted C3-C20 heteroaryl group, a substituted or unsubstituted C6-C20 condensed polycyclic group, a halogen atom, a cyano group, a nitro group, a hydroxy group, and a carboxy group;

p is an integer from 1 to 12; and

* is a binding site.

The compound represented by Formula 1 may include one of the compounds below.

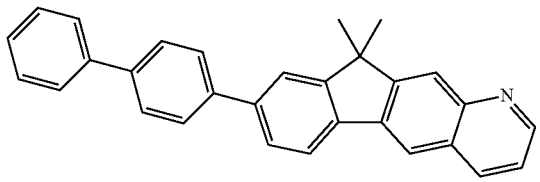

16

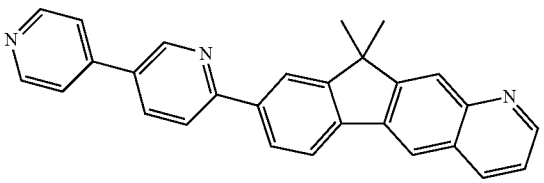

21

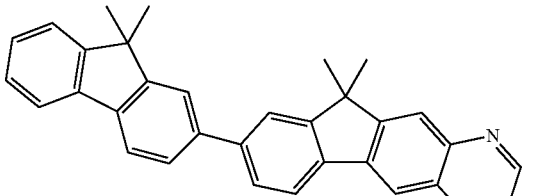

24

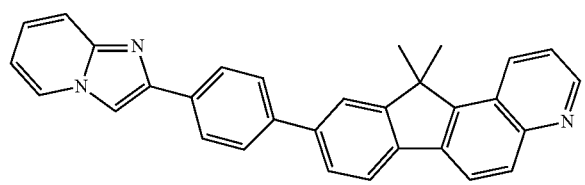

25

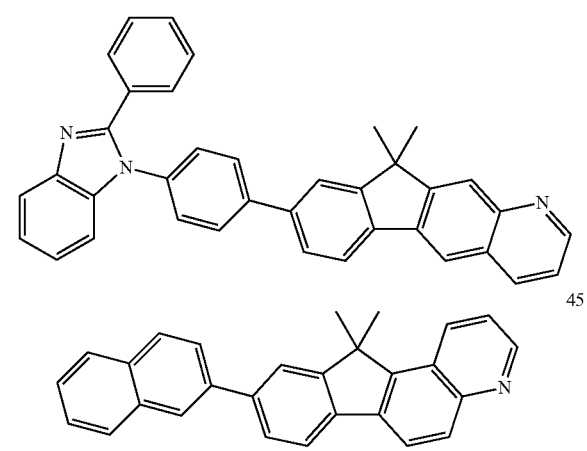

45

According to another aspect of the present invention, there is provided an organic light-emitting device including:

a first electrode;

a second electrode; and an organic layer interposed between the first electrode and the second electrode, wherein the organic layer includes a heterocyclic compound represented by Formula 1 or 2.

The organic layer may include a hole injection layer, a hole transport layer, a single layer having both hole injecting and transporting capabilities, an electron injection layer, an electron transport layer, or a single layer having both electron injecting and transporting capabilities.

The organic layer may be an emission layer, wherein the heterocyclic compound represented by Formula 1 or 2 is used as a host or a fluorescent dopant for a fluorescent or phosphorescent device.

The organic layer may include an emission layer, a hole transport layer, and an electron transport layer, wherein the emission layer further includes an anthracene compound, an arylamine compound, or a styryl compound.

The organic layer may include an emission layer, a hole transport layer, and an electron transport layer, wherein one of the red, green, blue, and white layers of the emission layer further includes a phosphorescent compound.

The organic layer may be a blue emission layer.

The organic layer may be a blue emission layer, wherein the compound represented by Formula 1 or 2 is used as a blue host.

The organic layer may include a plurality of layers, wherein at least one layer of the organic layer is formed by a wet process using a heterocyclic compound represented by Formula 1 or 2.

According to another aspect of the present invention, there is provided a flat panel display device including the organic light-emitting device, wherein a first electrode of the organic light-emitting device is electrically connected to a source electrode or a drain electrode of a thin film transistor.

BRIEF DESCRIPTION OF THE DRAWING

The embodiments will become apparent by describing in detail exemplary embodiments thereof with reference to the attached drawing in which:

FIG. 1 illustrates an organic light-emitting device according to an embodiment.

DETAILED DESCRIPTION

Hereinafter, the present invention will now be described more fully with reference to the accompanying drawing, in which an exemplary embodiment of the invention is shown.

Anthracene derivatives may be used as materials for forming an organic emission layer. PBD, PF-6P, and PyPySPyPy, as well as Alq3 may also be used as materials for forming an electron transport layer. For example, an organic light-emitting device may be manufactured using a compound of a phenylanthracene dimer or trimer. However, such organic light-emitting devices may have a narrow energy gap and low blue-light color purity since two or three oligomeric species of anthracene may be linked by conjugation.

In addition, such compounds may be highly vulnerable to oxidation and thus may be liable to produce impurities, thereby necessitating purification. Thus, organic light-emitting devices may be manufactured using an anthracene compound including naphthalene substituted for anthracene at 1,9 position or using a diphenylanthracene compound including an aryl group substituted for a phenyl group at an m-position. However, these organic light-emitting devices may have low light-emission efficiency.

In addition, organic light-emitting devices may be manufactured using a naphthalene-substituted monoanthracene derivative. However, the compound may have a low light-emission efficiency of about 1 cd/A, and thus, such organic light-emitting devices may not be suitable for practical use. Organic light-emitting devices may also be manufactured using compounds having a phenylanthracene structure. However, these compounds may be substituted with an aryl group at an m-position, and thereby may have a low light-emission efficiency of about 2 cd/A in spite of excellent thermal resistance.

According to an embodiment, a heterocyclic compound represented by Formula 1 or Formula 2, below, is provided.

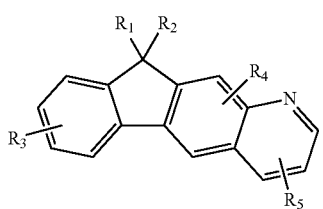

Formula 1

In Formula 1, $R_1$ to $R_5$ may each independently be selected from the group of a hydrogen atom, a heavy hydrogen atom, a substituted or unsubstituted C1-C60 alkyl group, a substituted or unsubstituted C2-C60 alkenyl group, a substituted or unsubstituted C2-C60 alkynyl group, a substituted or unsubstituted C3-C60 cycloalkyl group, a substituted or unsubstituted C1-C60 alkoxy group, a substituted or unsubstituted C5-C60 aryloxy group, a substituted or unsubstituted C5-C60 arylthio group, a substituted or unsubstituted C5-C60 aryl group, an amino group substituted with a C5-C60 aryl group or a C3-C60 heteroaryl group, a substituted or unsubstituted C3-C60 heteroaryl group, a substituted or unsubstituted C6-C60 condensed polycyclic group, a halogen atom, a cyano group, a nitro group, a hydroxy group, and a carboxy group.

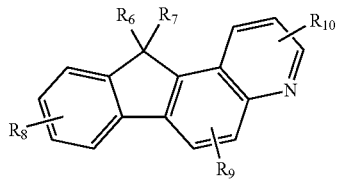

Formula 2

In Formula 2, $R_6$ to $R_{10}$ may each independently be selected from the group of a hydrogen atom, a heavy hydrogen atom, a substituted or unsubstituted C1-C60 alkyl group, a substituted or unsubstituted C2-C60 alkenyl group, a substituted or unsubstituted C2-C60 alkynyl group, a substituted or unsubstituted C3-C60 cycloalkyl group, a substituted or unsubstituted C1-C60 alkoxy group, a substituted or unsubstituted C5-C60 aryloxy group, a substituted or unsubstituted C5-C60 arylthio group, a substituted or unsubstituted C5-C60 aryl group, an amino group substituted with a C5-C60 aryl group or a C3-C60 heteroaryl group, a substituted or unsubstituted C3-C60 heteroaryl group, a substituted or unsubstituted C6-C60 condensed polycyclic group, a halogen atom, a cyano group, a nitro group, a hydroxy group, and a carboxy group.

The heterocyclic compounds of Formulae 1 and 2 may be suitable as a material for forming an emission layer, an electron transport layer, or an electron injection layer of an organic light-emitting device. The heterocyclic compounds of Formulae 1 and 2 having a heterocyclic group therein may have a high glass transition temperature (Tg) or a high melting point due to inclusion of the heterocyclic group. Thus, the heterocyclic compound may have high thermal resistance against Joule heat generated in an organic layer, between organic layers, or between an organic layer and a metallic electrode when light emission occurs, and may have high durability in a high-temperature environment.

An organic light-emitting device manufactured using the compound of Formula 1 or 2 may have high durability when stored or operated.

Substituents in the compounds of Formulae 1 and 2 will now be described in detail.

In an implementation, in Formulae 1 and 2, $R_1$ to $R_{10}$ may each independently be selected from the group of a hydrogen atom, a heavy hydrogen atom, a cyano group, a halogen atom, a substituted or unsubstituted C1-C20 alkyl group, a substituted or unsubstituted C5-C40 aryl group, a substituted or unsubstituted C3-C40 heteroaryl group, an amino group substituted with a C5-C40 aryl group or a C3-C20 heteroaryl group, and a substituted or unsubstituted C6-C40 condensed polycyclic group.

In another implementation, in Formulae 1 and 2, $R_1$ to $R_{10}$ may each independently be selected from the group of a hydrogen atom, a heavy hydrogen atom, a halogen atom, a cyano group, a C1-C20 alkyl group, and compounds represented by Formulae 2a to 2g below.

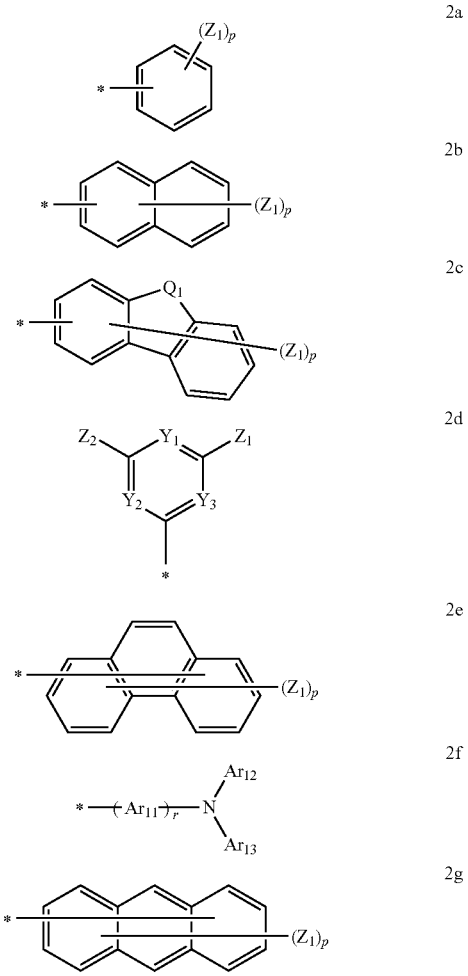

In Formulae 2a to 2g, $Q_1$ may be selected from the group of linking groups represented by —C($R_{11}$)($R_{12}$)—, —N($R_{13}$)—, —S—, and —O—;

$Y_1$, $Y_2$, and $Y_3$ may each independently be selected from the group of linking groups represented by —N= and —C($R_{14}$)=;

$Z_1$, $Z_2$, $Ar_{12}$, $Ar_{13}$, $R_{11}$, $R_{12}$, and $R_{13}$ may each independently be selected from the group of a hydrogen atom, a heavy hydrogen atom, a substituted or unsubstituted C1-C20 alkyl group, a substituted or unsubstituted C5-C20 aryl group, a substituted or unsubstituted C3-C20 heteroaryl group, a substituted or unsubstituted C6-C20 condensed polycyclic group, a halogen atom, a cyano group, a nitro group, a hydroxy group, and a carboxy group;

$Ar_{11}$ may be selected from the group of a substituted or unsubstituted C1-C20 alkylene group, a substituted or unsubstituted C5-C20 arylene group, and a substituted or unsubstituted C3-C20 heteroarylene group;

p may be an integer from 1 to 12; r may be an integer from 0 to 5; and * may be a binding site.

In another implementation, in Formulae 1 and 2, $R_1$ to $R_{10}$ may each independently be selected from the group of a hydrogen atom, a heavy hydrogen atom, a halogen atom, a cyano group, a methyl group, an ethyl group, a propyl group, a butyl group, a pentyl group, and compounds represented by Formulae 3a to 3d below.

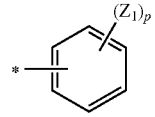

3a

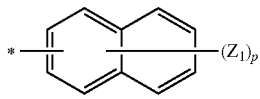

3b

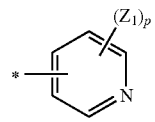

3c

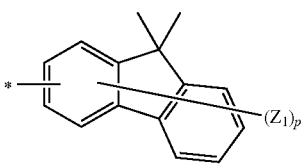

3d

In Formulae 3a to 3d, $Z_1$ may be selected from the group of a hydrogen atom, a heavy hydrogen atom, a substituted or unsubstituted C1-C20 alkyl group, a substituted or unsubstituted C5-C20 aryl group, a substituted or unsubstituted C3-C20 heteroaryl group, a substituted or unsubstituted C6-C20 condensed polycyclic group, a halogen atom, a cyano group, a nitro group, a hydroxy group, and a carboxy group;

p may be an integer from 1 to 12; and * may be a binding site.

In yet another implementation, in Formulae 1 and 2, $R_1$, $R_2$, $R_6$, and $R_7$ may each independently be selected from the group of a hydrogen atom, a heavy hydrogen atom, a substituted or unsubstituted C1-C20 alkyl group, a substituted or unsubstituted C5-C20 aryl group, and $R_3$, $R_4$, $R_5$, $R_8$, $R_9$, and $R_{10}$ are each independently selected from the group consisting of a hydrogen atom, a heavy hydrogen atom, a halogen atom, a cyano group, a C1-C20 alkyl group, and compounds represented by Formulae 2a to 2g below.

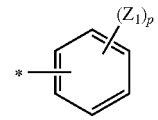

2a

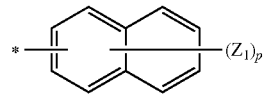

2b

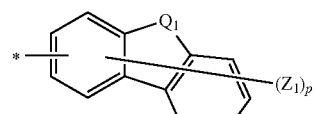

2c

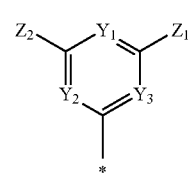

2d

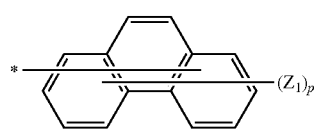

2e

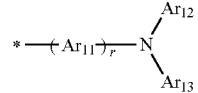

2f

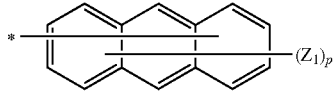

2g

In Formulae 2a to 2g, $Q_1$ may be selected from the group of linking groups represented by —$C(R_{11})(R_{12})$—, —$N(R_{13})$—, —S—, and —O—;

$Y_1$, $Y_2$, and $Y_3$ may each independently be selected from the group of linking groups represented by —N= and —$C(R_{14})$=;

$Z_1$, $Z_2$, $Ar_{12}$, $Ar_{13}$, $R_{11}$, $R_{12}$, and $R_{13}$ may each independently be selected from the group of a hydrogen atom, a heavy hydrogen atom, a substituted or unsubstituted C1-C20 alkyl group, a substituted or unsubstituted C5-C20 aryl group, a substituted or unsubstituted C3-C20 heteroaryl group, a substituted or unsubstituted C6-C20 condensed polycyclic group, a halogen atom, a cyano group, a nitro group, a hydroxy group, and a carboxy group;

$Ar_{11}$ may be selected from the group of a substituted or unsubstituted C1-C20 alkylene group, a substituted or unsubstituted C5-C20 arylene group, and a substituted or unsubstituted C3-C20 heteroarylene group;

p may be an integer from 1 to 12; r may be an integer from 0 to 5; and * may be a binding site.

In still another implementation, in Formulae 1 and 2, $R_1$, $R_2$, $R_4$, $R_5$, $R_6$, $R_7$, $R_9$, and $R_{10}$ may each independently be selected from the group of a hydrogen atom, a heavy hydrogen atom, a C1-C20 alkyl group, and a substituted or unsubstituted C5-C20 aryl group, and $R_3$ and $R_8$ are each independently selected from the group consisting of a hydrogen atom, a heavy hydrogen atom, a halogen atom, a cyano group, a methyl group, an ethyl group, a propyl group, a butyl group, a pentyl group, and compounds represented by Formulae 3a to 3d below.

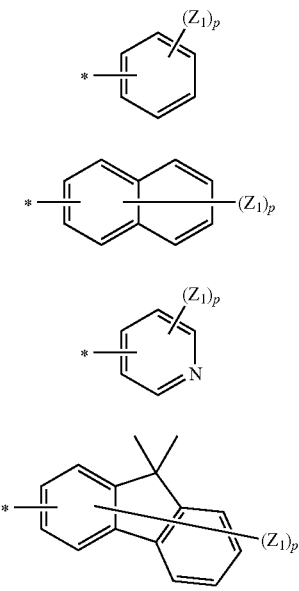

In Formulae 3a to 3d, $Z_1$ may be selected from the group of a hydrogen atom, a heavy hydrogen atom, a substituted or unsubstituted C1-C20 alkyl group, a substituted or unsubstituted C5-C20 aryl group, a substituted or unsubstituted C3-C20 heteroaryl group, a substituted or unsubstituted C6-C20 condensed polycyclic group, a halogen atom, a cyano group, a nitro group, a hydroxy group, and a carboxy group;

p may be an integer from 1 to 12; and * may be a binding site.

In still another implementation, in Formulae 1 and 2, $R_1$, $R_2$, $R_6$, and $R_7$ may each independently be a methyl group or a phenyl group, and $R_3$, $R_4$, $R_5$, $R_8$, $R_9$, and $R_{10}$ may each independently be selected from the group of a hydrogen atom, a heavy hydrogen atom, a halogen atom, a cyano group, a methyl group, an ethyl group, a propyl group, a butyl group, a pentyl group, and compounds selected from the group consisting of Formulae 3a to 3d below.

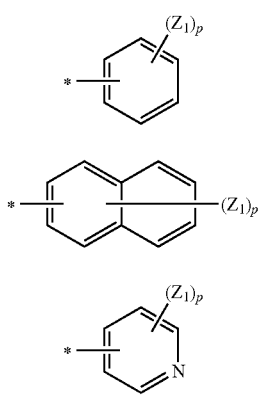

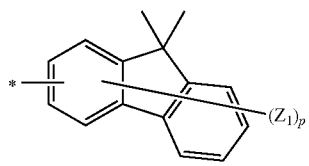

In Formulae 3a to 3d, $Z_1$ may be selected from the group of a hydrogen atom, a heavy hydrogen atom, a substituted or unsubstituted C1-C20 alkyl group, a substituted or unsubstituted C5-C20 aryl group, a substituted or unsubstituted C3-C20 heteroaryl group, a substituted or unsubstituted C6-C20 condensed polycyclic group, a halogen atom, a cyano group, a nitro group, a hydroxy group, and a carboxy group;

p may be an integer from 1 to 12; and * may be a binding site.

Hereinafter, substituents described with reference to Formulae 1 and 2 will now be described in detail. In this regard, the number of carbon atoms in substituents is presented only for illustrative purposes and does not limit the characteristics of the substituents.

The C1-C60 alkyl group used herein may be linear or branched. Examples of the alkyl group may include, but are not limited to, methyl, ethyl, propyl, isobutyl, sec-butyl, pentyl, iso-amyl, hexyl, heptyl, octyl, nonyl, and dodecyl. At least one hydrogen atom of the alkyl group may be substituted with a heavy hydrogen atom, a halogen atom, a hydroxyl group, a nitro group, a cyano group, an amino group, an amidino group, hydrazine, hydrazone, a carboxyl group or a salt thereof, a sulfonic acid group or a salt thereof, a phosphoric acid group or a salt thereof, a C1-C10 alkyl group, a C1-C10 alkoxy group, a C2-C10 alkenyl group, a C2-C10 alkynyl group, a C6-C16 aryl group, or a C4-C16 heteroaryl group.

The C2-C60 alkenyl group used herein may refer to a hydrocarbon chain having at least one carbon-carbon double bond at a center or at a terminal of the unsubstituted alkyl group. Examples of the C2-C60 alkenyl group may include ethenyl, propenyl, and butenyl. At least one hydrogen atom of the alkenyl group may be substituted with the same substituent groups as described above in connection with the alkyl group.

The C2-C60 alkynyl group used herein may refer to a hydrocarbon chain having at least one carbon-carbon triple bond at a center or at a terminal of the alkyl group. Examples of the C2-C60 alkynyl group may include acetylene, propylene, phenylacetylene, naphthylacetylene, isopropylacetylene, t-butylacetylene, and diphenylacetylene. At least one hydrogen atom of the alkynyl group may be substituted with the same substituent groups as described above in connection with the alkyl group.

The C3-C60 cycloalkyl group used herein may refer to a C3-C60 cyclic alkyl group wherein at least one hydrogen atom in the cycloalkyl group may be substituted with the same substituent group described above in connection with the C1-C60 alkyl group.

The C1-C60 alkoxy group used herein may be a group having a structure of —OA wherein A is a C1-C60 alkyl group as described above. Examples of the C1-C60 alkoxy group may include methoxy, ethoxy, propoxy, isopropyloxy, butoxy, and pentoxy. At least one hydrogen atom of the alkoxy group may be substituted with the same substituent groups as described above in connection with the alkyl group.

The C5-C60 aryl group used herein may refer to a carbocyclic aromatic system containing at least one ring. At least two rings may be fused to each other or linked to each other by a single bond. The term 'aryl' may refer to an aromatic system, such as phenyl, naphthyl, or anthracenyl. At least one hydrogen atom in the aryl group may be substituted with the same substituent groups described with reference to the C1-C60 alkyl group.

Examples of the substituted or unsubstituted C5-C60 aryl group may include a phenyl group, a C1-C10 alkylphenyl group (for example, ethylphenyl group), a halophenyl group (for example, o-, m-, and p-fluorophenyl group, dichlorophenyl group), a cyanophenyl group, dicyanophenyl group, a trifluoromethoxyphenyl group, a biphenyl group, a halobiphenyl group, a cyanobiphenyl group, a C1-C10 alkyl biphenyl group, a C1-C10 alkoxybiphenyl group, o-, m-, and p-tolyl groups, o-, m-, and p-cumenyl groups, a mesityl group, a phenoxyphenyl group, a (α,α-dimethylbenzene)phenyl group, a (N,N'-dimethyl)aminophenyl group, a (N,N'-diphenyl)aminophenyl group, a pentalenyl group, an indenyl group, a naphthyl group, a halonaphthyl group (for example, fluoronaphthyl group), a C1-C10 alkylnaphthyl group (for example, methylnaphthyl group), a C1-C10 alkoxynaphthyl group (for example, methoxynaphthyl group), a cyanonaphthyl group, an anthracenyl group, an azulenyl group, a heptalenyl group, an acenaphthylenyl group, a phenalenyl group, a fluorenyl group, an anthraquinolyl group, a methylanthryl group, a phenanthryl group, a triphenylene group, a pyrenyl group, a chrycenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronelyl group, a trinaphthylenyl group, a heptaphenyl group, a heptacenyl group, a pyranthrenyl group, and an ovalenyl group.

The C4-C60 heteroaryl group used herein may include one, two, or three hetero atoms selected from the group of N, O, P, and S. At least two rings may be fused to each other or linked to each other by a single bond. Examples of the C4-C60 heteroaryl group may include a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolinyl group, an isoquinolinyl group, and a dibenzothiophene group. In addition, at least one hydrogen atom in the heteroaryl group may be substituted with the same substituent groups described above with reference to the C1-C60 alkyl group.

The C5-C60 aryloxy group used herein may refer to a group represented by —OA$_1$, wherein A$_1$ is a C5-C60 aryl group. An example of the aryloxy group may include a phenoxy group. At least one hydrogen atom in the aryloxy group may be substituted with the same substituent groups described with reference to the C1-C60 alkyl group.

The C5-C60 arylthio group used herein may refer to a group represented by —SA$_1$, wherein A$_1$ is a C5-C60 aryl group. Examples of the arylthio group may include a benzenethio group and a naphthylthio group. At least one hydrogen atom in the arylthio group may be substituted with the substituent groups described with reference to the C1-C60 alkyl group.

The C6-C60 condensed polycyclic group may be a substituent including at lest two rings wherein at least one aromatic ring and/or at least one non-aromatic ring are fused to each other.

Examples of the compound represented by Formula 1 or 2 may include compounds represented by the following Compounds 1 through 57. However, the compound represented by Formula 1 or 2 is not limited thereto.

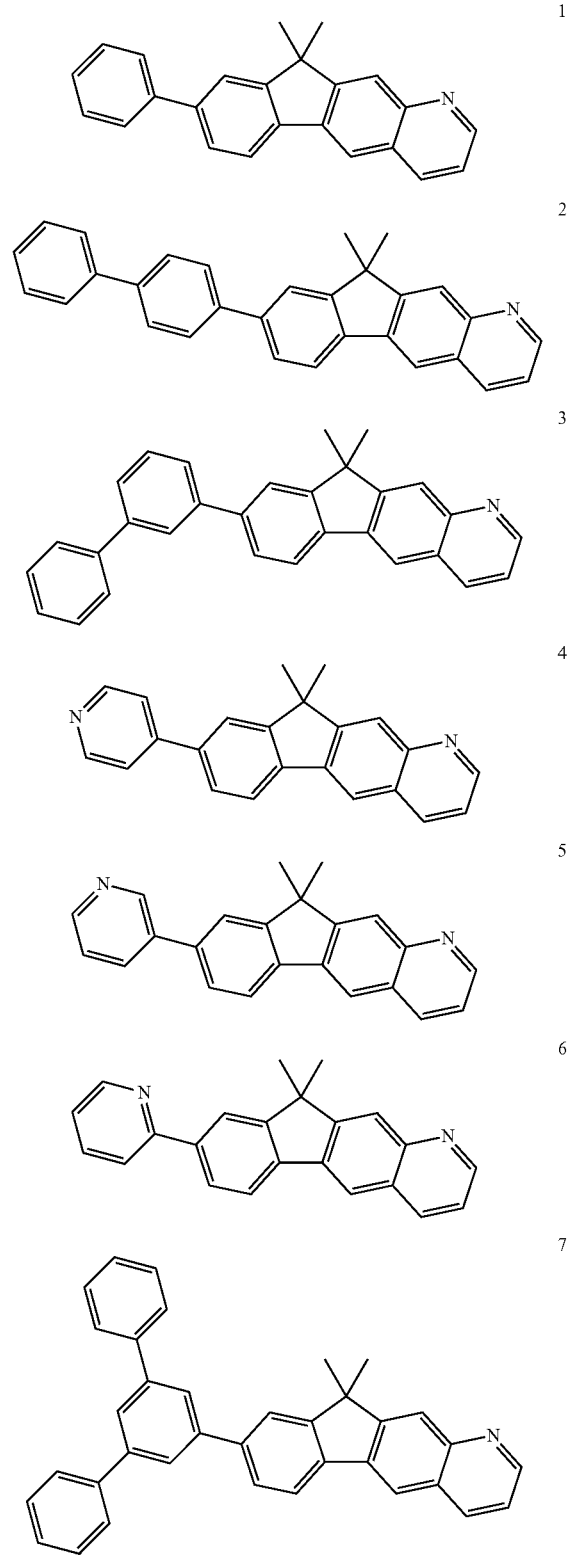

-continued
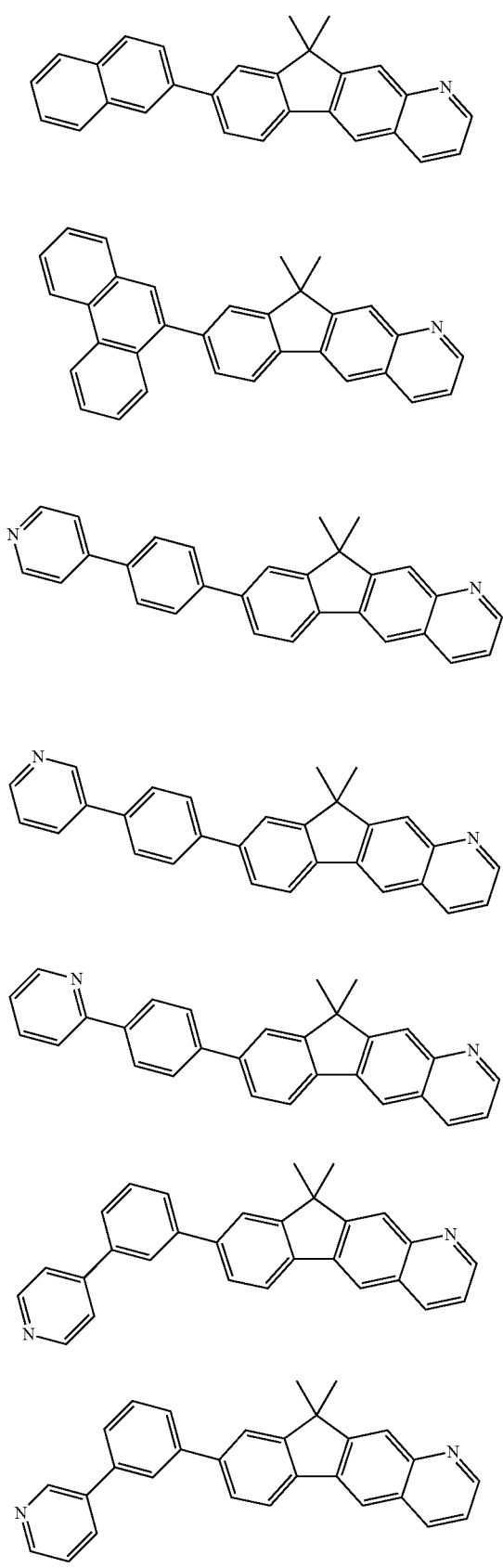
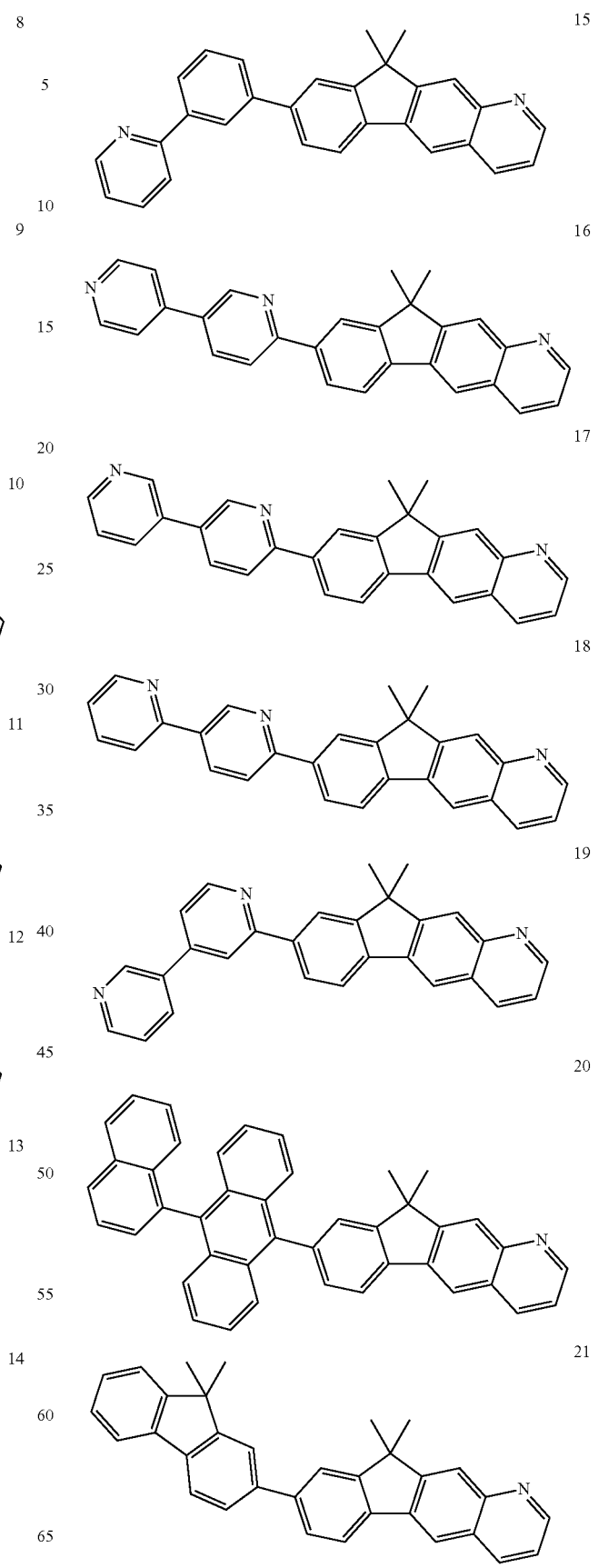

22
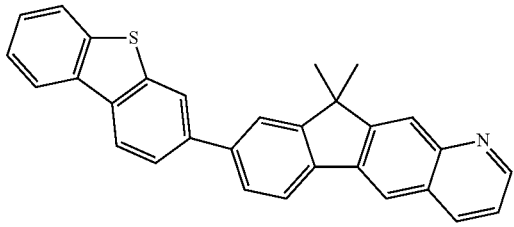
23
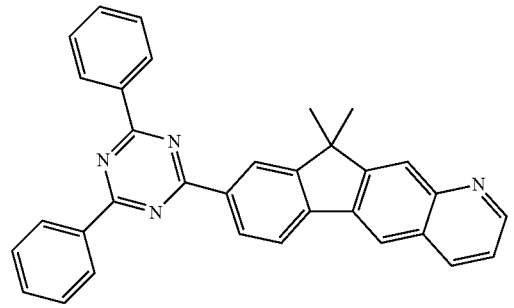
24
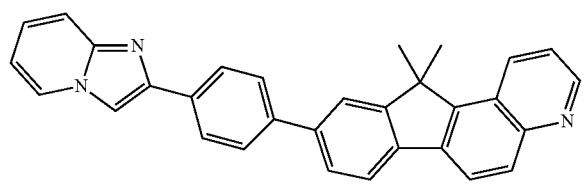
25
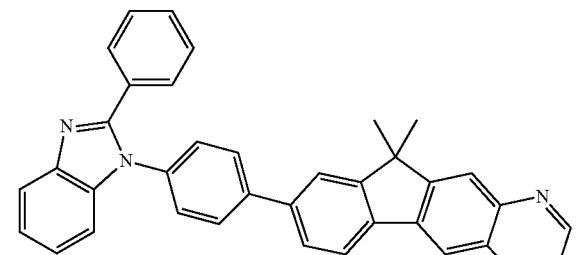
26
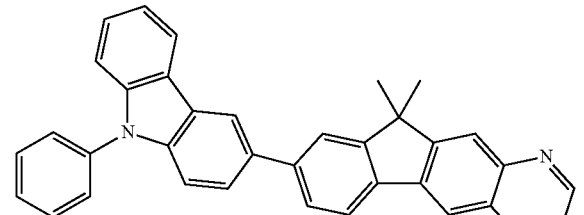
27
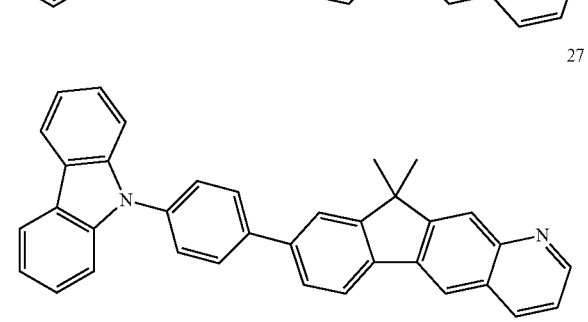
28
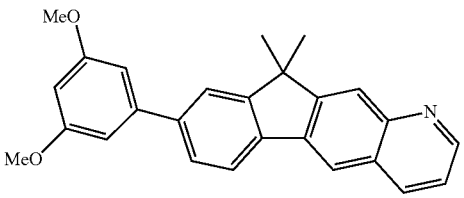
29
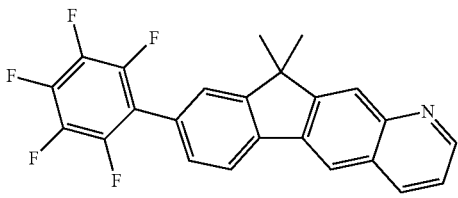
30
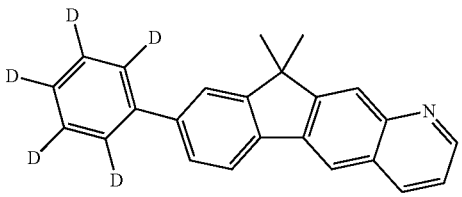
31
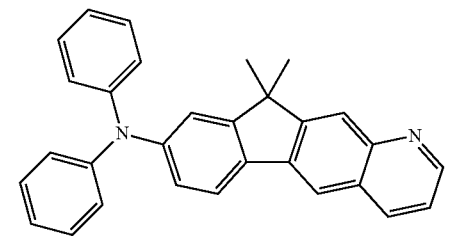
32
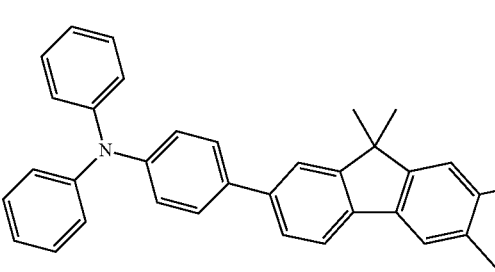
33
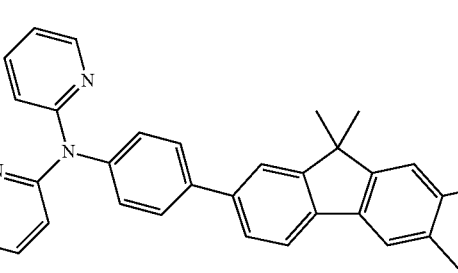
34
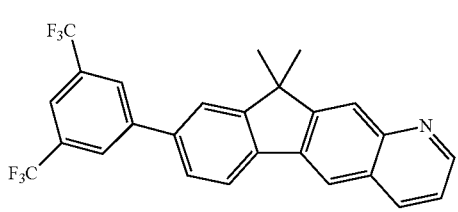

21
-continued
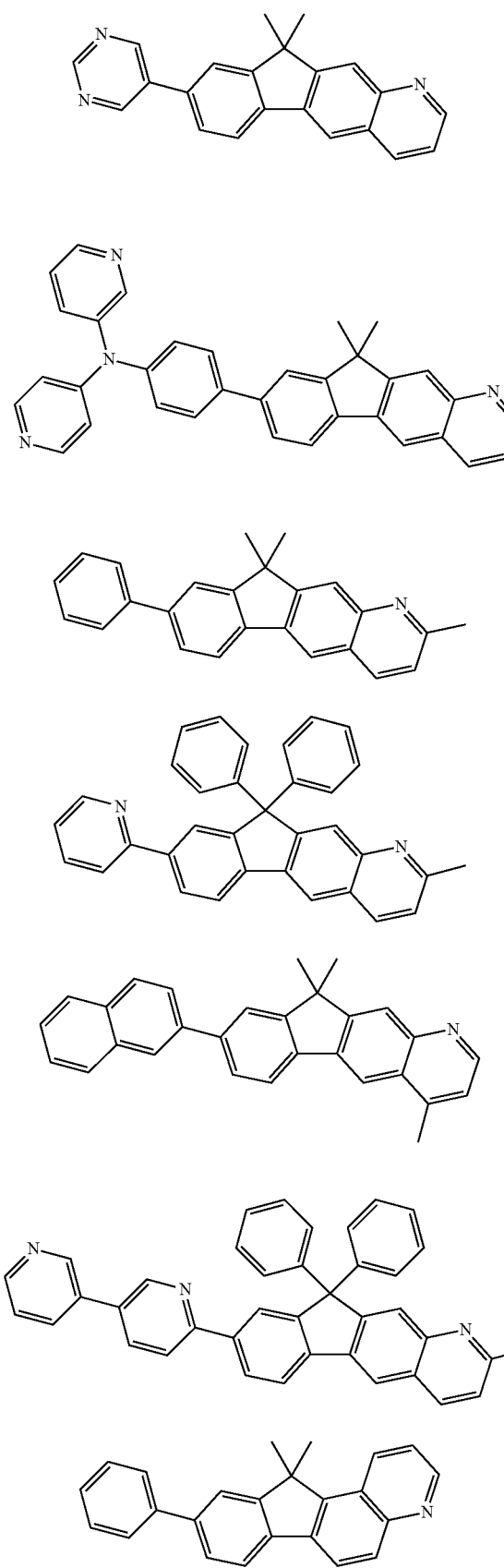
22
-continued
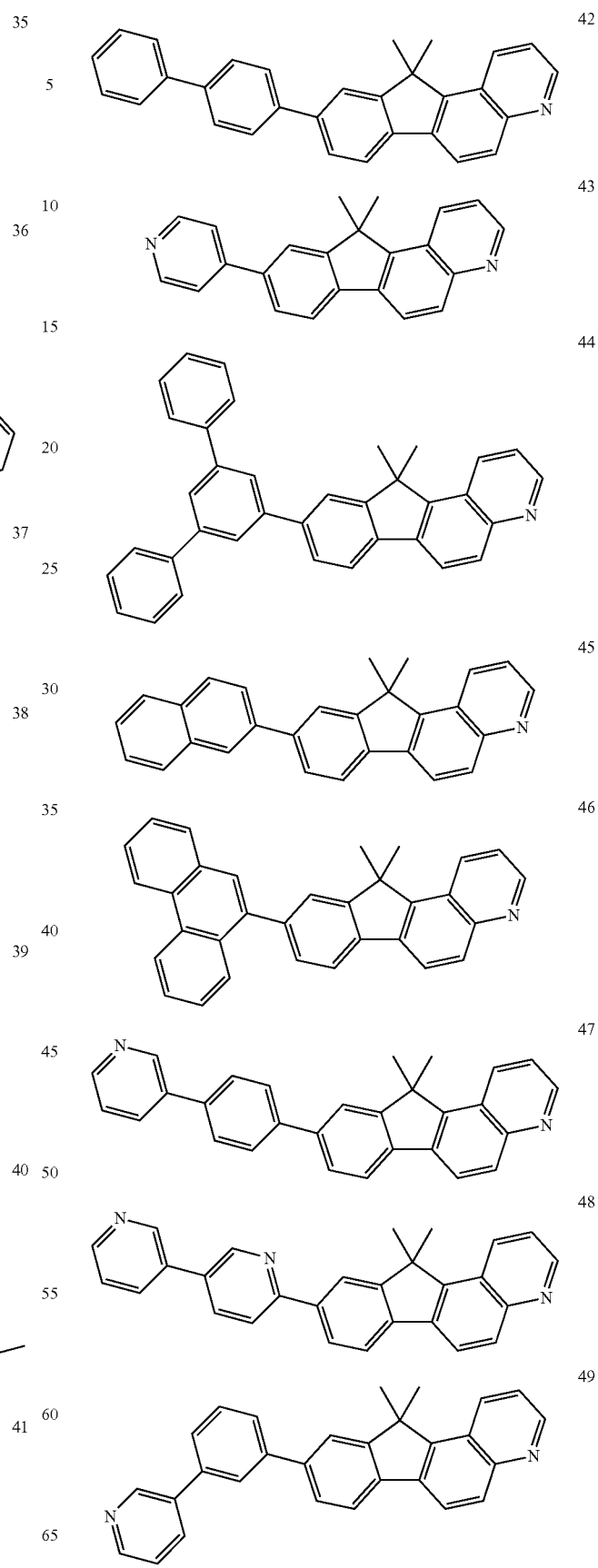

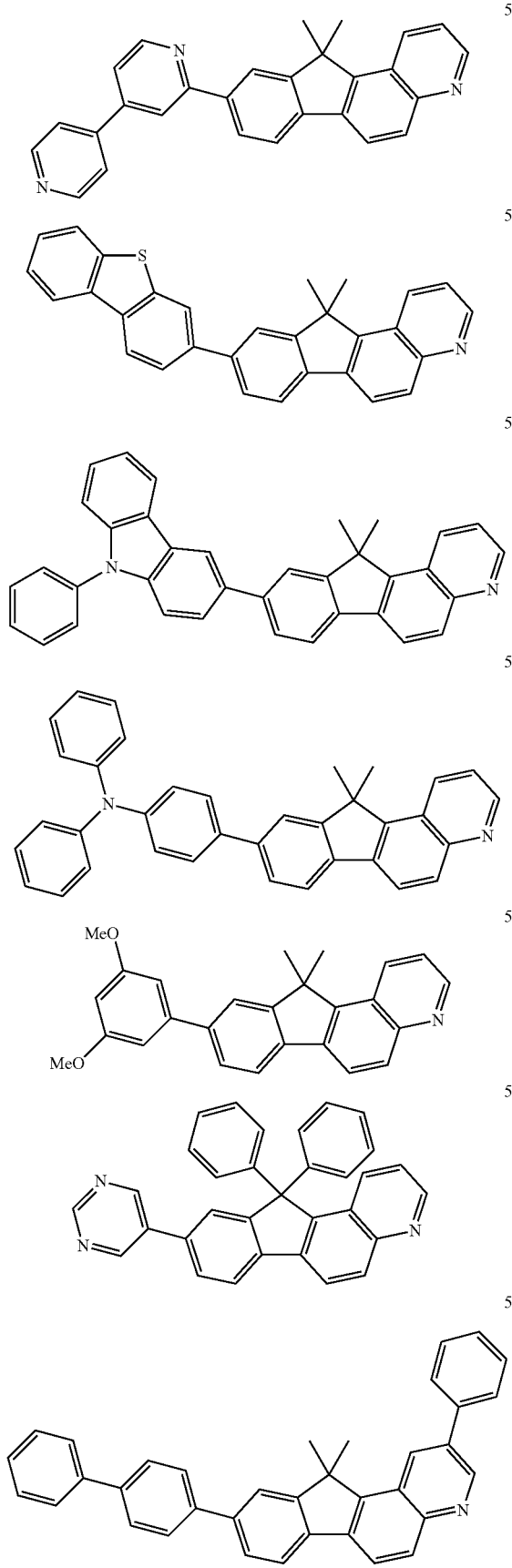

An organic light-emitting device according to an embodiment may include a first electrode, a second electrode, and an organic layer interposed between the first electrode and the second electrode. The organic layer may include the heterocyclic compound represented by Formula 1 or 2 described above.

The organic layer including the heterocyclic compound represented by Formula 1 or 2 may include a hole injection layer (HIL), a hole transport layer (HTL), a single layer having both hole injecting and hole transporting capabilities, an electron injection layer (EIL), an electron transport layer (ETL), or a single layer having both electron injecting and electron transporting capabilities.

Alternatively, the organic layer including the heterocyclic compound represented by Formula 1 or 2 may be an emission layer (EML); and the heterocyclic compound represented by Formula 1 or 2 may be used as a host or a dopant for a fluorescent or phosphorescent device.

According to the present embodiment, the organic layer of the organic light-emitting device may include an EML, an HTL, and an ETL. If the EML, the HTL, or the ETL includes the compound of Formula 1 or 2, the EML may include an anthracene compound, an arylamine compound, or a styryl compound.

At least one hydrogen atom of the anthracene compound, the arylamine compound, or the styryl compound may be substituted with the same substituent groups described above with reference to the C1-C60 alkyl group. The arylamine may refer to a C5-C60 arylamine group.

If the organic layer of the organic light-emitting device according to the present embodiment includes the EML, the HTL, and the ETL, and the EML, the HTL, or the ETL includes the compound of Formula 1 or 2, a red, green, blue, or white layer of the EML may include a phosphorescent compound.

The organic layer of the organic light-emitting device may be a blue EML. If the organic layer of the organic light-emitting device is a blue EML, the compound of Formula 1 or 2 may be used as a blue host.

The first electrode may be an anode; and the second electrode may be a cathode, but the reverse is also possible.

For example, the organic light-emitting device according to the present embodiment may have a structure of first electrode/HIL/EML/second electrode, a structure of first electrode/HIL/EML/ETL/second electrode, or a structure of first electrode/HIL/HTL/EML/ETL/EIL/second electrode. An organic light-emitting device may also have a structure of first electrode/single layer having both hole injecting and hole transporting capabilities/EML/ETL/second electrode, or a structure of first electrode/single layer having both hole injecting and hole transporting capabilities/EML/ETL/EIL/second electrode. The organic light-emitting device may also have a structure of first electrode/HTL/EML/single layer having both electron injecting and electron transporting capabilities/second electrode, a structure of first electrode/HIL/EML/single layer having both electron injecting and electron transporting capabilities/second electrode, or a structure of first electrode/HIL/HTL/EML/single layer having both electron injecting and electron transporting capabilities/second electrode.

The organic light-emitting device according to the present embodiment may be a top-emission type organic light-emitting device or a bottom-emission type organic light-emitting device.

Hereinafter, a method of manufacturing an organic light-emitting device, according to an embodiment will be described with reference to FIG. 1. Referring to FIG. 1, the organic light-emitting device may include a substrate, a first electrode (anode), a HIL, a HTL, an EML, an ETL, an EIL, and a second electrode (cathode).

First, the first electrode may be formed by depositing or sputtering a material for forming the first electrode having a high work function on a substrate. The first electrode may constitute an anode or a cathode. The substrate may be any substrate commonly used in organic light-emitting devices, and may be, for example, a glass substrate or a transparent plastic substrate with excellent mechanical strength, thermal stability, transparency, surface smoothness, ease of handling, and water resistance. The material for forming the first electrode may be indium tin oxide (ITO), indium zinc oxide (IZO), tin oxide ($SnO_2$), zinc oxide (ZnO), aluminum (Al), silver (Ag), magnesium (Mg), or the like, which has excellent conductivity, and may form a transparent or reflective electrode.

Then, a HIL may be formed on the first electrode by vacuum deposition, spin coating, casting, Langmuir Blodgett (LB) deposition, or the like.

When the HIL is formed using vacuum deposition, the deposition conditions may vary according to a compound that is used to form the HIL, and the structure and thermal characteristics of the HIL to be formed. For example, the deposition conditions may include a deposition temperature of 100 to 500° C., a vacuum pressure of $10^{-8}$ to $10^{-3}$ torr, and a deposition rate of 0.01 to 100 Å/sec.

When the HIL is formed using spin coating, coating conditions may vary according to a compound that is used to form the HIL, and the structure and thermal properties of the HIL to be formed. For example, the coating conditions may include a coating speed of about 2000 rpm to about 5000 rpm, and a thermal treatment temperature of about 80° C. to about 200° C., wherein the thermal treatment is for removing a solvent after coating.

The HIL may be formed of any material that is commonly used to form a HIL. Examples of the material may include a phthalocyanine compound such as copper phthalocyanine, 4,4',4''-tris(3-methylphenylphenylamino)triphenylamine (m-MTDATA), N,N'-di(1-naphthyl)-N,N'-diphenylbenzidine (NPB), TDATA, 2T-NATA, polyaniline/dodecylbenzenesulfonic acid (Pani/DBSA), poly(3,4-ethylenedioxythiophene)/poly(4-styrenesulfonate) (PEDOT/PSS), polyaniline/camphor sulfonicacid (Pani/CSA), and (polyaniline)/poly(4-styrenesulfonate (PANI/PSS), but are not limited thereto.

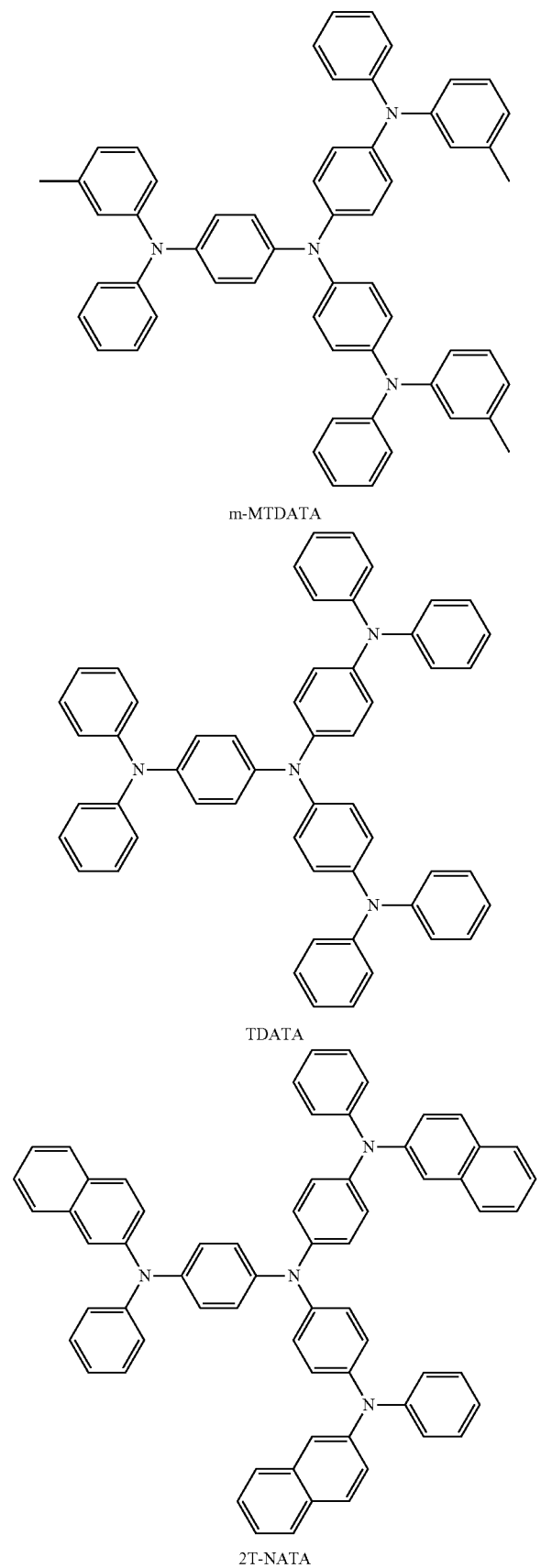

m-MTDATA

TDATA

2T-NATA

A thickness of the HIL may be about 100 to 10,000 Å, e.g., 100 to 1,000 Å. When the HIL has a thickness within the above range, the HIL may have excellent hole injecting characteristics without an increase in driving voltage.

Then, the HTL may be formed on the HIL using various methods, for example by vacuum deposition, spin coating, casting, and LB deposition. When the HTL is formed using vacuum deposition or spin coating, the deposition or coating conditions may be similar to those applied to form the HIL, although the deposition or coating conditions may vary according to a material used to form the HTL.

The material for forming the HTL may include the heterocyclic compound of Formula 1 or 2 or any known hole transporting material. Examples of such hole transporting materials may include, but are not limited to, carbazole derivatives such as N-phenylcarbazole or polyvinylcarbazole, and amine derivatives having an aromatic condensed ring, such as NPB, N,N'-bis(3-methylphenyl)- N,N'-diphenyl-[1,1-biphenyl]-4,4'-diamine (TPD), or the like.

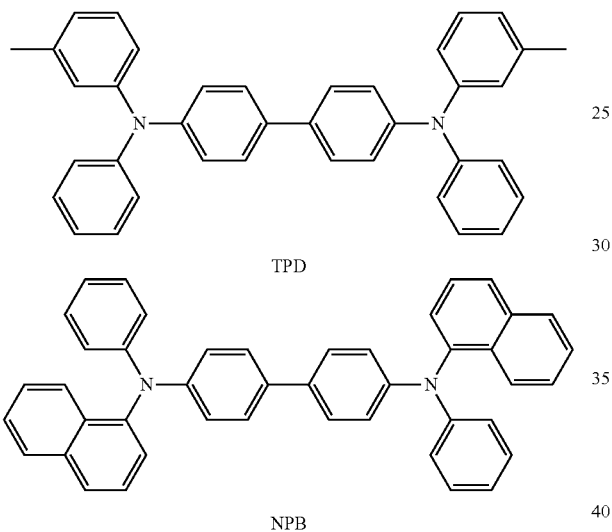

The HTL may have a thickness of about 50 Å to about 1,000 Å, e.g., about 100 Å to about 600 Å. When the HTL has a thickness within the above range, the HTL may have excellent hole transporting characteristics without a substantial increase in driving voltage.

Then, the EML may be formed on the HTL using various methods, for example, vacuum deposition, spin coating, casting, and LB deposition. When the EML is formed using vacuum deposition or spin coating, the deposition or coating conditions may be similar to those applied to form the HIL, although the deposition and coating conditions may vary according to a material that is used to form the EML.

The EML may include the heterocyclic compound of Formula 1 or 2 described above. For example, the heterocyclic compound of Formula 1 or 2 may be used as a host or a dopant. The EML may be formed using a variety of well-known light-emitting materials, in addition to the heterocyclic compound of Formula 1 or 2. The EML may also be formed using a well-known host and dopant. The dopant for forming the EML may include either a fluorescent dopant or a phosphorescent dopant, which are widely known in the art.

Examples of the host may include Alq3, 4,4'-N,N'-dicarbazole-biphenyl (CBP), poly(n-vinylcarbazole) (PVK), 9,10-di(naphthalene-2-yl)anthracene (ADN), TCTA, 1,3,5-tris(N-phenylbenzimidazole-2-yl)benzene (TPBI), 3-tert-butyl-9,10-di-2-naphthylanthracene (TBADN), E3, and distyrylarylene (DSA), but are not limited thereto.

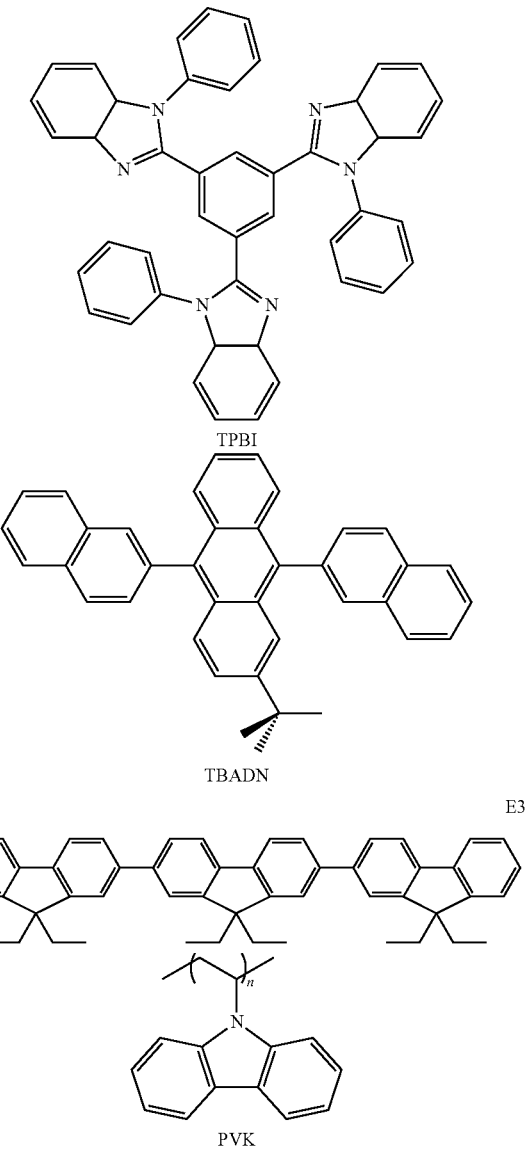

Examples of red dopants may include platinum(II) octaethylporphyrin (PtOEP), Ir(piq)$_3$, Btp$_2$Ir(acac), and DCJTB, but are not limited thereto.

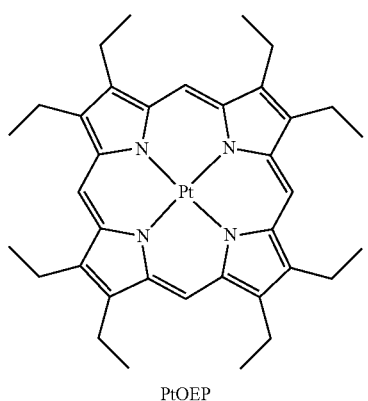

PtOEP

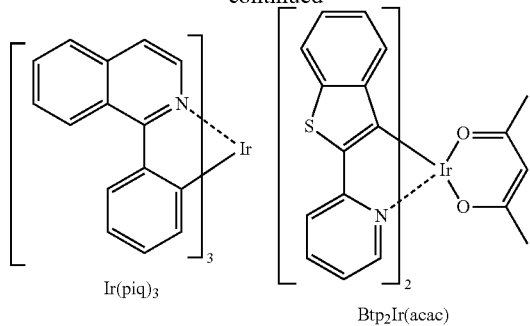

Ir(piq)₃    Btp₂Ir(acac)

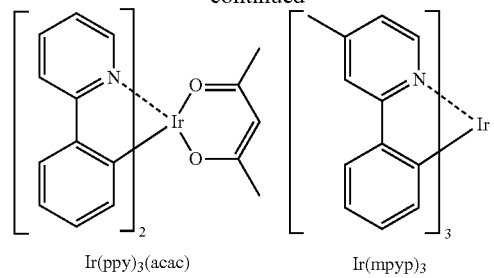

Ir(ppy)₃(acac)    Ir(mpyp)₃

Examples of green dopants may include Ir(ppy)₃ (where "ppy" denotes phenylpyridine), Ir(ppy)₂(acac), Ir(mpyp)₃, and C545T, but are not limited thereto.

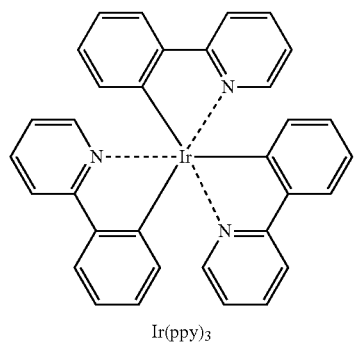

Ir(ppy)₃

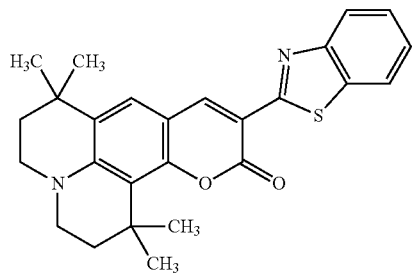

C545T

Examples of the blue dopant may include the heterocyclic compound represented by Formula 1 or 2. Alternatively, examples of well-known blue dopants include F₂Irpic, (F₂ppy)₂Ir(tmd), Ir(dfppz)₃, ter-fluorene, 4,4'-bis(4-diphenylaminostyryl)biphenyl (DPAVBi), and 2,5,8,11-tetra-t-butyl pherylene (TBPe), but are not limited thereto.

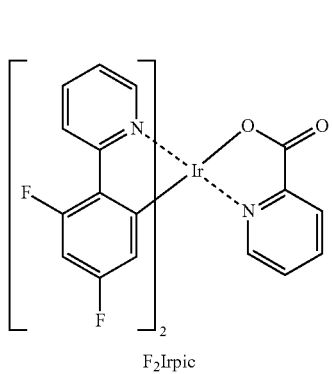

F₂Irpic

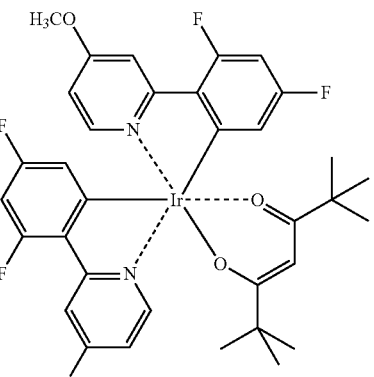

(F₂ppy)₂Ir(tmd)

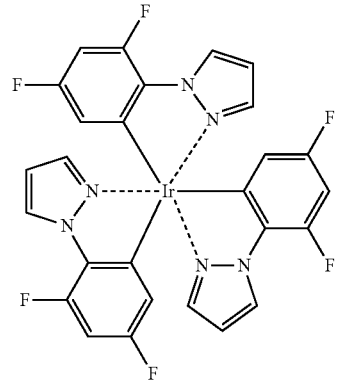

Ir(dfppz)₃

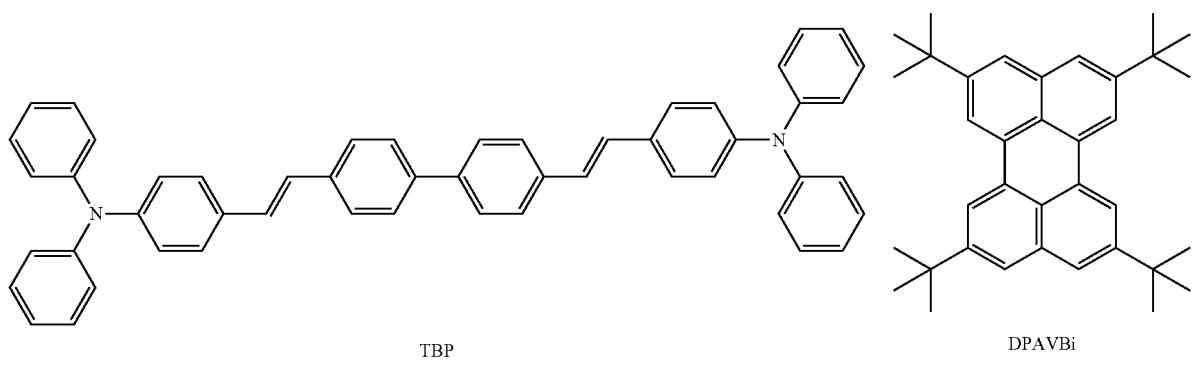

TBP    DPAVBi

An amount of the dopant may be in a range of about 0.1 to about 20 parts by weight, or about 0.5 to about 12 parts by weight, based on 100 parts by weight of the EML material (which is equivalent to the total weight of the host and the dopant). When the amount of the dopant is within the above range, concentration quenching may be substantially prevented.

The EML may have a thickness of about 100 Å to about 1,000 Å, e.g., about 200 Å to about 600 Å. When the EML has a thickness within the above range, the EML may have excellent light-emitting characteristics without a substantial increase in driving voltage.

When the EML includes a phosphorescent dopant, a hole blocking layer (HBL) (not shown in FIG. 1) may be formed on the EML in order to prevent diffusion of triplet excitons or holes into the ETL. In this case, the HBL may be formed of any material that is commonly used to form a HBL, without limitation. Examples of such HBL materials may include oxadiazole derivatives, triazole derivatives, phenathroline derivatives, Balq, and BCP.

The HBL may have a thickness of about 50 Å to about 1,000 Å, e.g., about 100 Å to about 300 Å. When the thickness of the HBL is within the range described above, the HBL may have excellent hole blocking characteristics without a substantial increase in driving voltage.

Then, the ETL may be formed on the EML (or HBL) using various methods, for example, by vacuum deposition, spin coating, casting, or the like. When the ETL is formed using vacuum deposition or spin coating, the deposition or coating conditions may be similar to those applied to form the HIL, although the deposition and coating conditions may vary according to the material that is used to form the ETL.

The electron transporting material may include the heterocyclic compound of Formula 1 or 2 described above. Alternatively, the ETL may be formed of any material that is widely known in the art. Examples of electron transporting materials may include quinoline derivatives, such as tris(8-quinolinolate)aluminum (Alq3), TAZ, or Balq, but are not limited thereto.

The ETL may have a thickness of about 100 Å to about 1,000 Å, e.g., about 100 Å to about 500 Å. When the ETL has a thickness within the above range, the ETL may have excellent electron transporting characteristics without a substantial increase in driving voltage.

In addition, the EIL, which may facilitate injection of electrons from the cathode, may be formed on the ETL.

Alternatively, materials, such as LiF, NaCl, CsF, $Li_2O$, or BaO, may be used to form the EIL. The deposition or coating conditions for forming the EIL may be similar to those applied to form the HIL, although the deposition and coating conditions may vary according to the material that is used to form the EIL.

The EIL may have a thickness of about 1 Å to 100 Å, e.g., about 5 Å to about 90 Å. When the EIL has a thickness within the above range, the EIL may have excellent electron injecting characteristics without a substantial increase in driving voltage.

Finally, the second electrode may be formed on the EIL using, for example, vacuum deposition, sputtering, or the like. The second electrode may constitute a cathode or an anode. The material for forming the second electrode may include a metal, an alloy, or an electrically conductive compound, materials which have a low work function, or a mixture thereof. In an implementation, the second electrode may be formed of lithium (Li), magnesium (Mg), aluminum (Al), aluminum (Al)-lithium (Li), calcium (Ca), magnesium (Mg)-indium (In), magnesium (Mg)-silver (Ag), or the like. In addition, in order to manufacture a top-emission type organic light-emitting device, a transparent cathode formed of a transparent material such as ITO or IZO may be used as the second electrode.

The organic light-emitting device according to the present embodiment may be included in various types of flat panel display devices, such as a passive matrix organic light-emitting display device or an active matrix organic light-emitting display device. In particular, when the organic light-emitting device is included in an active matrix organic light-emitting display device including a thin-film transistor, the first electrode formed on the substrate may function as a pixel electrode, electrically connected to a source electrode or a drain electrode of the thin-film transistor. Moreover, the organic light-emitting device may also be included in a flat panel display device having a double-sided screen.

If the organic light-emitting device according to the present embodiment includes a plurality of organic layers, at least one of the organic layers may be formed of the heterocyclic compound of Formula 1 or 2 by using a deposition process or a wet process of coating a solution of the heterocyclic compound of Formula 1 or 2.

Hereinafter, the present invention will be described in detail with reference to synthesis examples of Compounds 2, 16, 21, 24, 25, and 45 and other examples. However, it will be understood that the embodiments are not limited to the particular details described. Further, the Comparative Examples are set forth to highlight certain characteristics of certain embodiments, and are not to be construed as either limiting the scope of the invention as exemplified in the Examples or as necessarily being outside the scope of the invention in every respect.

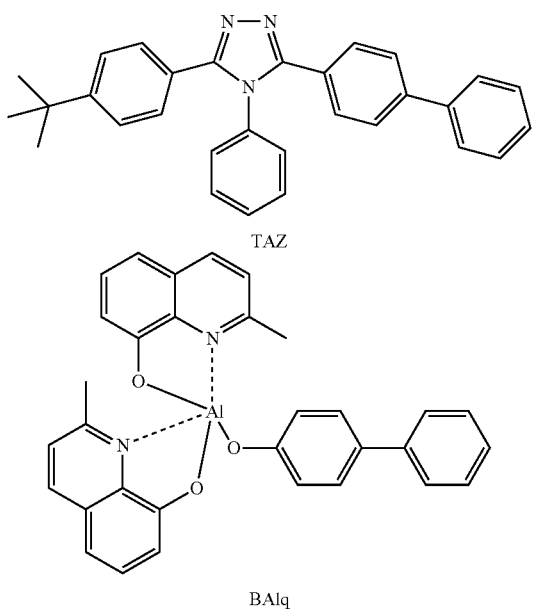

TAZ

BAlq

EXAMPLES

Synthesis Example 1

Synthesis of Compound 2

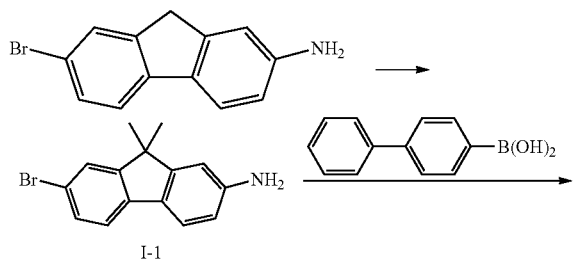

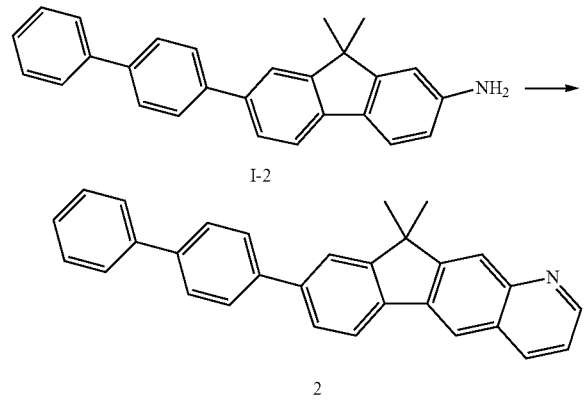

Synthesis of Intermediate I-1

5.2 g (20 mmol) of 2-amino-7-bromofluorene and 0.18 g (1 mmol) of triethylbenzylammonium salt were dissolved in 50 mL of a mixture of DMSO and a 50% sodium hydroxide solution (1:1). 6.25 g (44 mmol) of methyl iodide was added thereto, and the mixture was stirred for 10 hours. 50 mL of water was added thereto, and the mixture was subjected to extraction three times with 50 mL of ethyl ether. An organic layer was collected and dried using magnesium sulfate to evaporate the solvent. The residue was separately purified using silica gel column chromatography to obtain 4.84 g of Intermediate I-1 (Yield: 84%). The produced compound was identified using LC-MS. $C_{15}H_{14}BrN:M^+$ 398.19

Synthesis of Intermediate I-2

5.76 g (20 mmol) of Intermediate I-1, 3.56 g (18 mmol) of 4-biphenyl borate, and 1.156 g (1 mmol) of $Pd(PPH_3)_4$ were dissolved in 100 mL of a toluene/2M sodium carbonate solution (4:1). The mixture was stirred at 100° C. for 12 hours. The mixture was cooled to room temperature and subjected to extraction three times with 100 mL of water and 100 mL of diethyl ether. An organic layer was collected and dried using magnesium sulfate to evaporate the solvent. The residue was separately purified using silica gel column chromatography to obtain 5.13 g of Intermediate I-2 (Yield: 79%). The produced compound was identified using LC-MS. $C27H_{23}N:M^+$ 362.19

Synthesis of Compound 2

5 g (13.8 mmol) of Intermediate I-2 and 10 g of a 70% sulfuric acid solution were added to 4 g of nitrobenzene. The mixture was heated to 110° C., and 10 g of glycerol, as an oxidant, was added thereto in drops. Then, the mixture was stirred at 110° C. for 10 hours. The mixture was cooled to room temperature and subjected to extraction three times with 50 mL of water and 50 mL of diethyl ether. An organic layer was collected and dried using magnesium sulfate to evaporate the solvent. The residue was separately purified using silica gel column chromatography to obtain 3.4 g of Compound 2 (Yield: 62%). The produced compound was identified using LC-MS and NMR. $C_{30}H_{23}N_1:M^+$ 398.19

$^1$H NMR (CDCl$_3$, 400 MHz) δ (ppm) 8.78 (d, 1H), 8.07-7.20 (m, 16H), 1.67 (s, 6H)

Synthesis Example 2

Synthesis of Compound 16

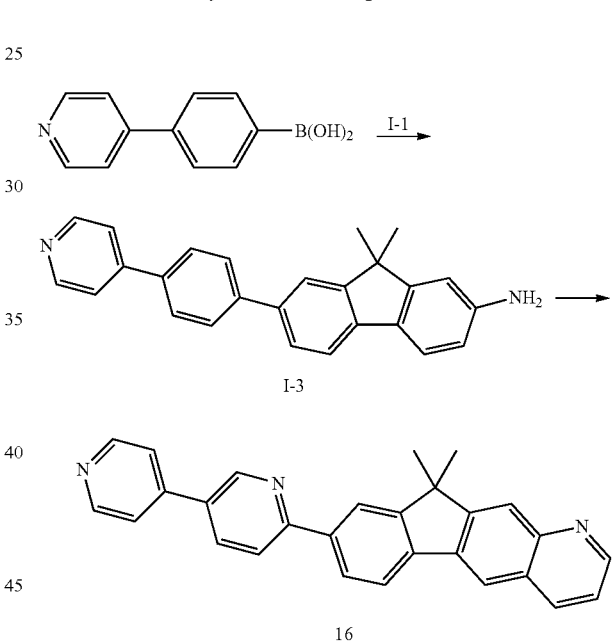

Synthesis of Intermediate I-3

5.35 g of Intermediate I-3 was synthesized with a yield of 82% in the same manner as the synthesis of Intermediate I-2, using 4-(4-bromophennyl)-pyridine borate and Intermediate I-1. The produced compound was identified using LC-MS. $C_{26}H_{22}N_2:M^+$ 363.18

Synthesis of Compound 16

3.69 g of Compound 16 was synthesized with a yield of 67% in the same manner as the synthesis of Compound 2, using Intermediate 1-3, sulfuric acid, nitrobenzene, and glycerol. The produced compound was identified using LC-MS and NMR. $C_{28}H_{21}N_3:M^+$ 400.18

$^1$H NMR (CDCl$_3$, 400 MHz) δ (ppm) 8.78 (d, 1H), 8.76 (s, 1H), 8.66 (d, 2H), 8.02-7.26 (m, 11H), 1.67 (s, 6H)

Synthesis Example 3

Synthesis of Compound 21

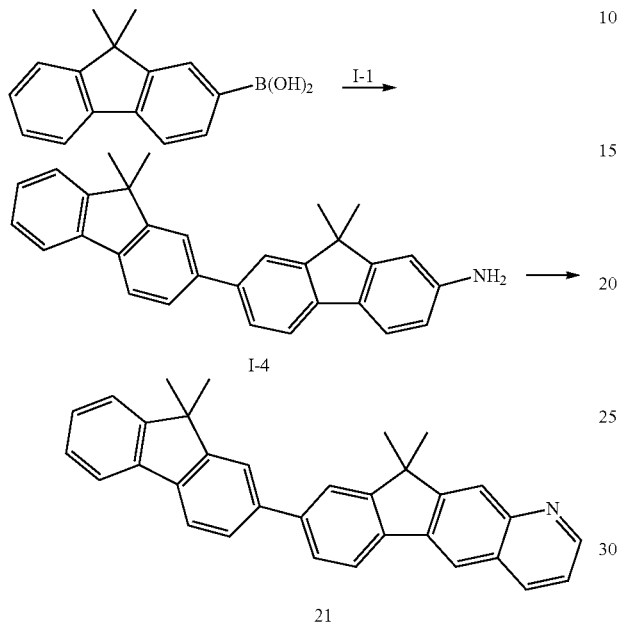

Synthesis of Intermediate I-4

5.34 g of Intermediate I-4 was synthesized with a yield of 74% in the same manner as the synthesis of Intermediate I-2 using 2-bromo-9,9-dimethyl borate and Intermediate I-1. The produced compound was identified using LC-MS. C$_{30}$H$_{27}$N$_1$: M$^+$ 402.22

Synthesis of Compound 21

3.62 g of Compound 21 was synthesized with a yield of 60% in the same manner as the synthesis of Compound 2, using Intermediate 1-4, sulfuric acid, nitrobenzene, and glycerol. The produced compound was identified using LC-MS and NMR. C$_{33}$H$_{27}$N$_1$:M$^+$ 438.22

$^1$H NMR (CDCl$_3$, 400 MHz) δ (ppm) 8.78 (d, 1H), 8.14-7.26 (m, 14H), 1.67-1.65 (m, 12H)

Synthesis Example 4

Synthesis of Compound 24

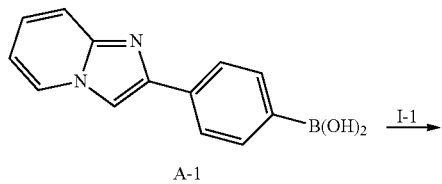

A-1

-continued

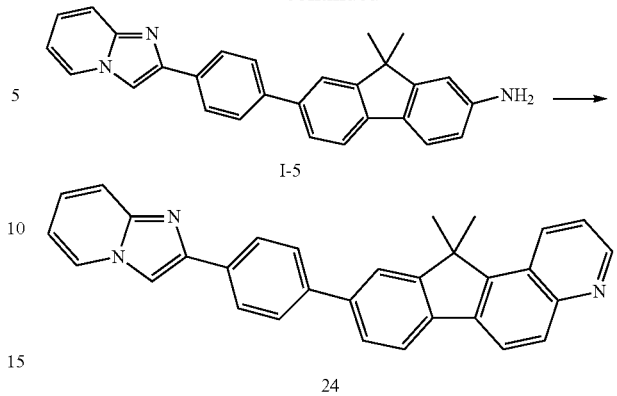

Synthesis of Intermediate I-5

5.20 g of Intermediate I-5 was synthesized with a yield of 72% in the same manner as the synthesis of Intermediate I-2, using a borate having A-1 structure and Intermediate I-5. The produced compound was identified using LC-MS. C$_{28}$H$_{23}$N$_3$: M+402.19

Synthesis of Compound 24

1.93 g of Compound 24 was synthesized with a yield of 32% in the same manner as the synthesis of Compound 2, using Intermediate 1-5, sulfuric acid, nitrobenzene, and glycerol. The produced compound was identified using LC-MS and NMR. C$_{31}$H$_{23}$N$_1$:M$^+$ 438.19

$^1$H NMR (CDCl$_3$, 400 MHz) δ (ppm) 8.78 (d, 1H), 8.09-7.26 (m, 14H), 7.01 (m, 1H), 6.61 (m, 1H), 1.67 (s, 6H)

Synthesis Example 5

Synthesis of Compound 25

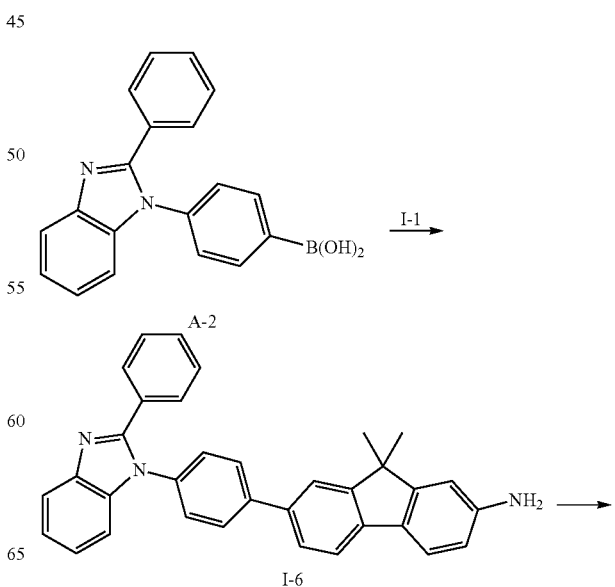

-continued

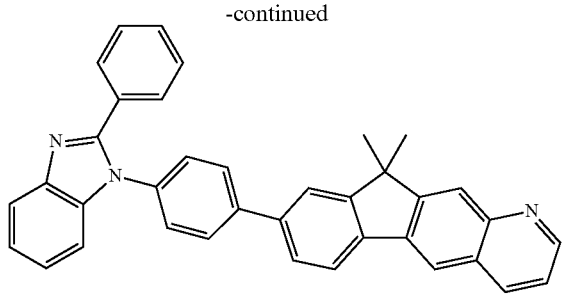

25

Synthesis of Intermediate I-6

6.88 g of Intermediate I-6 was synthesized with a yield of 80% in the same manner as the synthesis of Intermediate I-2, using a borate having A-2 structure and Intermediate I-1. The produced compound was identified using LC-MS. $C_{34}H_{27}N_3$:$M^+$ 478.22

Synthesis of Compound 25

4.32 g of Compound 25 was synthesized with a yield of 61% in the same manner as the synthesis of Compound 2, using Intermediate 1-6, sulfuric acid, nitrobenzene, and glycerol. The produced compound was identified using LC-MS and NMR. $C_{37}H_{27}N_3$:$M^+$ 515.23

$^1$H NMR (CDCl$_3$, 400 MHz) δ (ppm) 8.78 (d, 1H), 8.11-7.22 (m, 20H), 1.67 (s, 6H)

Synthesis Example 6

Synthesis of Compound 45

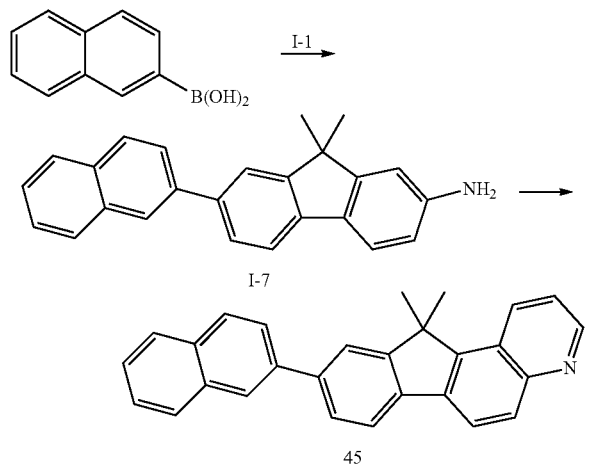

Synthesis of Intermediate I-7

4.95 g of Intermediate I-7 was synthesized with a yield of 83% in the same manner as the synthesis of Intermediate I-2, using 2-naphthyl borate and Intermediate I-1. The produced compound was identified using LC-MS. $C_{25}H_{21}N_1$:$M^+$ 336.17

Synthesis of Compound 45

1.48 g of Compound 45 was synthesized with a yield of 29% in the same manner as the synthesis of Compound 2, using Intermediate 1-7, sulfuric acid, nitrobenzene, and glycerol. The produced compound was identified using LC-MS and NMR. $C_{28}H_{21}N_1$:$M^+$ 515.23

$^1$H NMR (CDCl$_3$, 400 MHz) δ (ppm) 8.76 (d, 1H), 8.10-7.22 (m, 14H), 1.67 (s, 6H)

Example 1

An anode was prepared by cutting a Corning 15 Ω/cm² (1200 Å) ITO glass substrate to a size of 50 mm×50 mm×0.7 mm, ultrasonically cleaning the glass substrate using isopropyl alcohol and pure water for five minutes each, and then irradiating UV light for 30 minutes and exposing to ozone to clean. Then, the anode was disposed in a vacuum deposition apparatus.

Then, 2-TNATA, which is a known material for forming a HIL, was vacuum deposited on the glass substrate to form a HIL having a thickness of 600 Å, and then 4,4'-bis[N-(1-naphthyl)-N-phenylamino]biphenyl (NPB), as a hole transporting compound, was vacuum deposited on the HIL to form a HTL having a thickness of 300 Å.

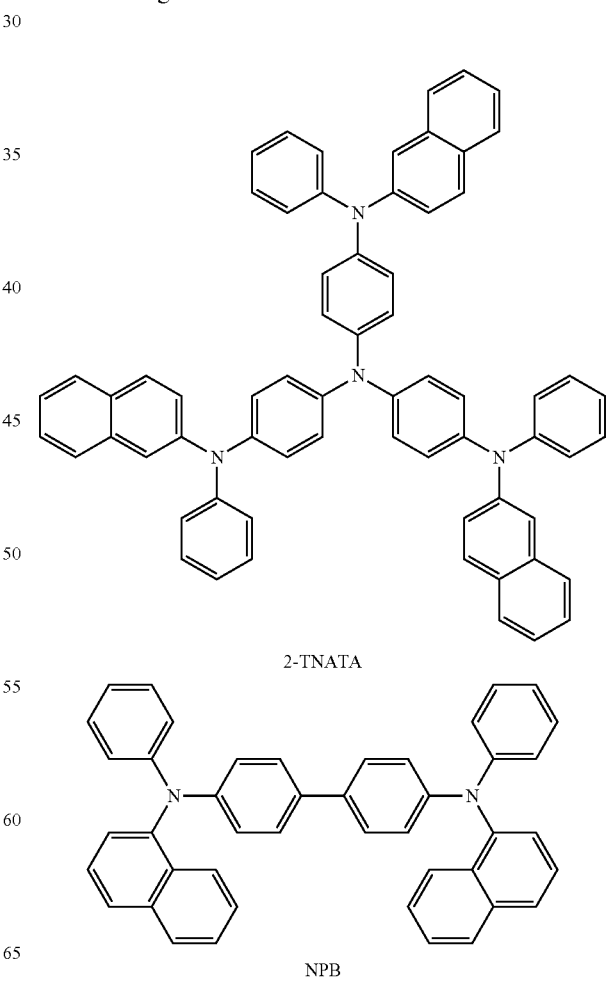

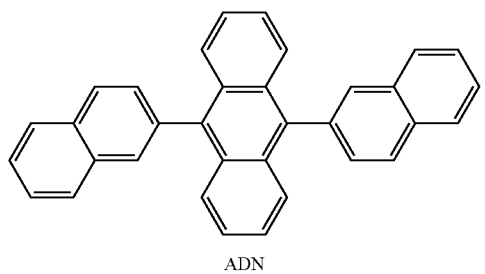

ADN

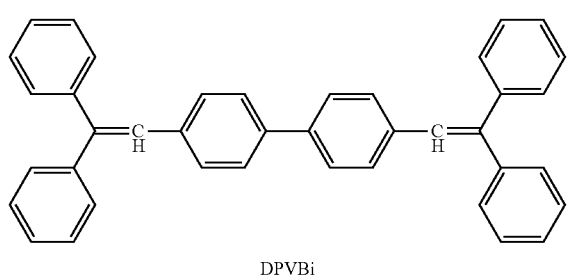

DPVBi

Then, Compound 2, as a blue fluorescent host, and 1,4-bis(2,2-diphenylvinyl)biphenyl (DPVBi), as a known blue fluorescent dopant, were deposited simultaneously with a weight ratio of 98:2, on the HTL, to form an EML having a thickness of 300 Å.

Then, Alq3 was deposited on the EML to form an ETL having a thickness of 300 Å, and then LiF, which is a halogenated alkali metal, was deposited on the ETL to form an EIL having a thickness of 10 Å. Then, Al was vacuum deposited on the EIL to form a cathode having a thickness of 3,000 Å, thereby forming a LiF/Al electrode. As a result, an organic light-emitting device was manufactured.

Example 2

An organic light-emitting device was manufactured in the same manner as in Example 1, except that Compound 45 was used instead of Compound 2 to form the EML.

Example 3

An organic light-emitting device was manufactured in the same manner as in Example 1, except that Compound 21 was used instead of Compound 2 to form the EML.

Example 4

An organic light-emitting device was manufactured in the same manner as in Example 1, except that a known host ADN and a known dopant DPVBi were used to form the EML and Compound 16 was used instead of Alq3 to form the ETL on the EML.

Example 5

An organic light-emitting device was manufactured in the same manner as in Example 4, except that Compound 24 was used instead of Compound 16 to form the ETL.

Example 6

An organic light-emitting device was manufactured in the same manner as in Example 4, except that Compound 25 was used instead of Compound 16 to form the ETL.

Example 7

An organic light-emitting device was manufactured in the same manner as in Example 1, except that Compound 16 was used instead of Alq3 to form the ETL.

Example 8

An organic light-emitting device was manufactured in the same manner as in Example 7, except that Compound 25 was used instead of Compound 16 to form the ETL.

Comparative Example 1

An organic light-emitting device was manufactured in the same manner as in Example 1, except that a known blue fluorescent host ADN was used instead of Compound 2 to form the EML.

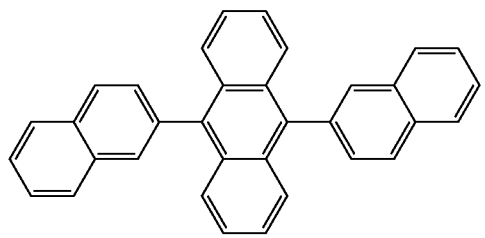

ADN

When the compound represented by Formula 1 or 2 according to an embodiment was used as a host and an electron transporting material of the organic light-emitting device, driving voltage of the organic light-emitting device was reduced by 1 V or more than ADN and Alq3 which are known materials, efficiency was considerably increased, thereby providing excellent I-V-L characteristics, and increasing a lifespan. When the compound according to an embodiment was used as a host of the organic light-emitting devices prepared in Examples 1 to 3, driving voltage was reduced by 1 V or more, efficiency was increased, and lifespan was increased compared to the organic light-emitting device of Comparative Example 1. In addition, if the compound according to an embodiment was used as an electron transporting material in the organic light-emitting devices prepared in Examples 4 to 6, driving voltage was reduced by 1.3 V or more than that of Comparative Example 1. When the compound according to an embodiment was used as a host of the EML and an electron transporting material, driving voltage was reduced by 1.7 V or more, efficiency was increased by about 200%, and lifespan was increased by 100% or more compared to the organic light-emitting device of Comparative Example 1. Characteristics and lifespan of the organic light-emitting devices are shown in Table 1 below.

TABLE 1

| | Host or electron transporting material | Driving voltage (V) | Current density (mA/cm$^2$) | Brightness (Cd/A) | Efficiency (Cd/A) | Color | Half-life span (hr @100 mA/cm$^2$) |
|---|---|---|---|---|---|---|---|
| Example 1 | Compound 2 | 6.25 | 50 | 2,335 | 4.67 | blue | 192 hr |
| Example 2 | Compound 45 | 6.17 | 50 | 2,415 | 4.83 | blue | 208 hr |
| Example 3 | Compound 21 | 6.33 | 50 | 2,385 | 4.77 | blue | 220 hr |
| Example 4 | Compound 16 | 5.73 | 50 | 2,470 | 4.94 | blue | 174 hr |
| Example 5 | Compound 24 | 6.06 | 50 | 2,571 | 5.14 | blue | 191 hr |
| Example 6 | Compound 25 | 5.84 | 50 | 2,903 | 5.80 | blue | 183 hr |
| Example 7 | Compound 2, Compound 16 | 5.61 | 50 | 3,135 | 6.27 | blue | 242 hr |
| Example 8 | Compound 2, Compound 25 | 5.54 | 50 | 3,205 | 6.41 | blue | 261 hr |
| Comparative Example 1 | ADN | 7.35 | 50 | 1,574 | 3.14 | blue | 120 hr |

The heterocyclic compounds according to the embodiments may exhibit excellent light-emitting characteristics and excellent electron transporting characteristics, and thus may be used as electron injecting materials or electron transporting materials suitable for all-color fluorescent and phosphorescent devices, such as red, green, blue, and white fluorescent and phosphorescent devices. For example, the heterocyclic compounds may be efficiently used as light-emitting materials of green, blue, and white fluorescent devices. By using the heterocyclic compounds, organic light-emitting devices having high efficiency, low driving voltage, high brightness, and long lifespan may be prepared.

By way of summation and review, an anthracene derivative may be used as a material for the organic emission layer. However, organic light-emitting devices including such an organic emission material may not have satisfactory life span, efficiency, and power consumption characteristics.

The embodiments provide a heterocyclic compound having improved electrical characteristics, charge transporting capabilities, and light-emission capabilities.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A heterocyclic compound represented by Formula 1 or Formula 2 below:

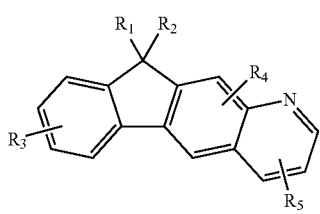

Formula 1

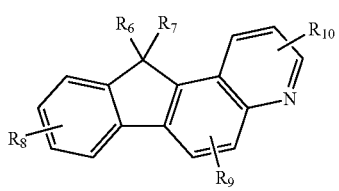

Formula 2 wherein:

$R_1$, $R_2$, $R_6$, and $R_7$ are each independently a methyl group or a phenyl group, and $R_3$, $R_4$, $R_5$, $R_8$, $R_9$, and $R_{10}$ are each independently selected from the group of a hydrogen atom, a heavy hydrogen atom, a halogen atom, a cyano group, a methyl group, an ethyl group, a propyl group, a butyl group, a pentyl group, and compounds selected from the group of Formulae 3a to 3d below:

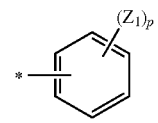

3a

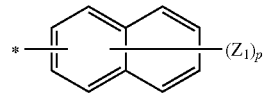

3b

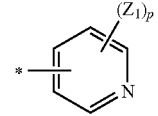

3c

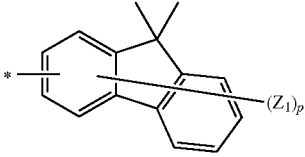

3d wherein $Z_1$ is selected from the group of a hydrogen atom, a heavy hydrogen atom, a substituted or unsubstituted C1-C20 alkyl group, a substituted or unsubstituted C6-C20 aryl group, a substituted or unsubstituted C3-C20 heteroaryl group, a substituted or unsubstituted C6-C20 condensed polycyclic group, a halogen atom, a cyano group, a nitro group, a hydroxy group, and a carboxy group;

p is an integer from 1 to 5 in Formula 3a, an integer from 1 to 7 in Formula 3b and 3d, and an integer from 1 to 4 in Formula 3c; and

*is a binding site.

2. A heterocyclic compound represented by Compound 2, 16, 21, 24, 25, or 45, below:

2

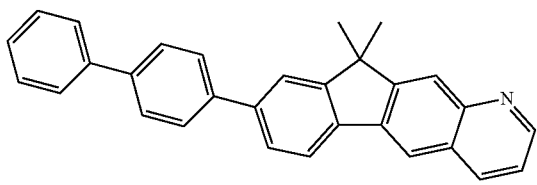

16

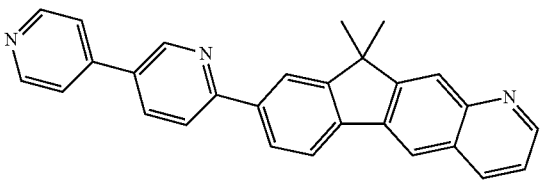

21

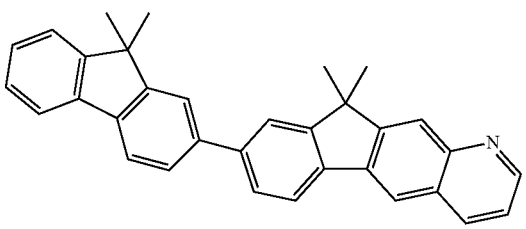

24

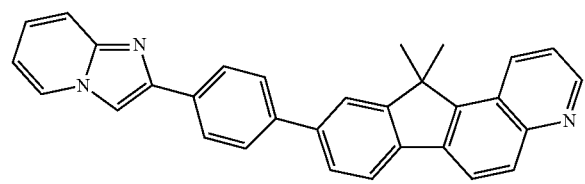

25

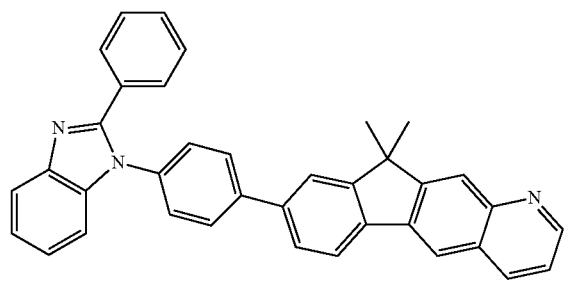

45

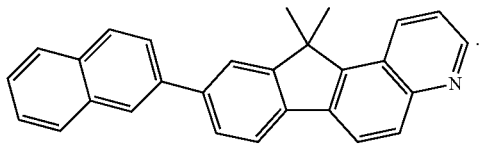

3. An organic light-emitting device, comprising:
a first electrode;
a second electrode; and
an organic layer interposed between the first electrode and the second electrode,
wherein the organic layer includes the heterocyclic compound as claimed in claim 1.

4. The organic light-emitting device of claim 3, wherein the organic layer includes a hole injection layer, a hole transport layer, a single layer having both hole injecting and transporting capabilities, an electron injection layer, an electron transport layer, or a single layer having both electron injecting and transporting capabilities.

5. The organic light-emitting device of claim 3, wherein the organic layer is an emission layer and the heterocyclic compound is a host or dopant for a fluorescent or phosphorescent device.

6. The organic light-emitting device of claim 3, wherein:
the organic layer includes an emission layer, a hole transport layer, and an electron transport layer, and the emission layer includes an anthracene compound, an arylamine compound, or a styryl compound.

7. The organic light-emitting device of claim 3, wherein:
the organic layer includes an emission layer, a hole transport layer, and an electron transport layer, and
one of a red, a green, a blue, and a white layer of the emission layer includes a phosphorescent compound.

8. The organic light-emitting device of claim 3, wherein the organic layer is a blue emission layer.

9. The organic light-emitting device of claim 3, wherein:
the organic layer is a blue emission layer, and
the heterocyclic compound is a blue host.

10. The organic light-emitting device of claim 3, wherein:
the organic layer includes a plurality of layers, and
at least one layer of the organic layers is formed by a wet process using the heterocyclic compound.

11. A flat panel display device comprising the organic light-emitting device as claimed in claim 3, wherein the first electrode of the organic light-emitting device is electrically connected to a source electrode or a drain electrode of a thin film transistor.

12. An organic light-emitting device, comprising:
a first electrode;
a second electrode; and
an organic layer interposed between the first electrode and the second electrode,
wherein the organic layer includes the heterocyclic compound as claimed in claim 2.

13. A flat panel display device comprising the organic light-emitting device as claimed in claim 12, wherein the first electrode of the organic light-emitting device is electrically connected to a source electrode or a drain electrode of a thin film transistor.

* * * * *